US008921429B2

(12) United States Patent
Akala et al.

(10) Patent No.: US 8,921,429 B2
(45) Date of Patent: Dec. 30, 2014

(54) BIODEGRADABLE STEALTH POLYMERIC PARTICLES FABRICATED USING THE MACROMONOMER APPROACH BY FREE RADICAL DISPERSION POLYMERIZATION

(75) Inventors: Emmanuel Akala, Mitchellville, MD (US); Simeon Adesina, Lanham, MD (US)

(73) Assignee: Howard University, Washington, DC (US)

( * ) Notice: Subject to any disclaimer, the term of this patent is extended or adjusted under 35 U.S.C. 154(b) by 161 days.

(21) Appl. No.: 12/952,843

(22) Filed: Nov. 23, 2010

(65) Prior Publication Data

US 2012/0129797 A1 May 24, 2012

(51) Int. Cl.

| | | |
|---|---|---|
| A61K 47/30 | (2006.01) | |
| C08G 63/06 | (2006.01) | |
| C08G 63/08 | (2006.01) | |
| C08G 63/60 | (2006.01) | |
| C08G 63/66 | (2006.01) | |
| B82Y 40/00 | (2011.01) | |
| A61K 31/704 | (2006.01) | |
| A61K 31/337 | (2006.01) | |
| B82Y 5/00 | (2011.01) | |
| A61K 9/51 | (2006.01) | |
| B82Y 15/00 | (2011.01) | |

(52) U.S. Cl.
CPC . B82Y 5/00 (2013.01); B82Y 40/00 (2013.01); A61K 31/704 (2013.01); A61K 31/337 (2013.01); A61K 9/5153 (2013.01); B82Y 15/00 (2013.01); Y10S 977/773 (2013.01)
USPC ......... 514/772.3; 525/437; 525/450; 977/773

(58) Field of Classification Search
None
See application file for complete search history.

(56) References Cited

U.S. PATENT DOCUMENTS

| | | | |
|---|---|---|---|
| 5,130,479 | A | 7/1992 | Ulbrich et al. |
| 6,828,025 | B2 | 12/2004 | Ali et al. |
| 2002/0064513 | A1 | 5/2002 | Maitra et al. |
| 2003/0018128 | A1 | 1/2003 | Wang et al. |
| 2005/0169957 | A1 | 8/2005 | Hossainy |

FOREIGN PATENT DOCUMENTS

| | | |
|---|---|---|
| WO | 2005/025736 A1 | 3/2005 |
| WO | 2007/074476 A1 | 7/2007 |

OTHER PUBLICATIONS

Pan et al. Journal of Biomedical Materials Research Part A, Apr. 2008, 89(1); 160-7.*
Danhier et al. Journal of Controlled Release 133 (2009) 11-17, published 2008.*
McGee J. Paul, Stanley S. Davis, Derek T. O'Hagan, Zero order release of protein from poly (D,L-lactide-co-glycolide) microparticles prepared using a modified phase separation technique, Journal of Controlled Release, 34, 77-86 (1995).
Nair S. Lakshmi and Cato T. Laurencin, Biodegradable polymers as biomaterials, Progress in Polymer Science, 32, 762-98 (2007).
Merkli A., C. Tabatabay, R. Gurny, J. Heller, Biodegradable polymers for the controlled release of ocular drugs, Progress in Polymer Science, 23, 563-80 (1998).
Ray Biswajit and Broja M. Mandal, Dispersion polymerization of Acrylamide: Part II. 2,2"-Azobisisobutyronitrile initiator, Journal of Polymer Science: Part A: Polymer Chemistry, 37, 493-499 (1999).
Horak Daniel, Effect of reaction parameters on the particle size in the dispersion polymerization of 2-Hydroxyethyl Methacrylate, Journal of Polymer Science Part A: Polymer Chemistry, 37, 3785-92 (1999).
Horak Daniel and Ostap Chaykivskyy, Poly (2-Hydroxyethyl Methacrylate-co-N,O-Dimethacryloylhydroxylamine) particles by dispersion polymerization, Journal of Polymer Science: Part A: Polymer Chemistry, 40, 1625-1632 (2002).
Gref. R., A. Domb, P. Quellec, T. Blunk, R. H. Muller, J. M. Verbavatz, R. Langer, The controlled intravenous delivery of drugs using PEG-coated sterically stabilized nanospheres, Advanced Drug Delivery Reviews, 16, 215-33 (1995).
Errico Cesare, Bartoli Cristina, Chiellini Federica and Chiellini Emo, Poly(hydroxyalkanoates)-based Polymeric Nanoparticles for Drug Delivery, Journal of Biomedicine and Biotechnology, 2009, Article ID 571702, 1-10 pages (2009).
Herault Damien, Christine Saluzzo, Marc Lemaire, Preparation of monodisperse enantiomerically pure glycidyl methacrylate-ethylene glycol dimethacrylate copolymers in dispersion copolymerization: Functionalization, Reactive and Functional Polymers, 66, 567-77 (2006).
Song, Jing-She, Frederic Tronc, Mitchell A. Winnik, Monodisperse, controlled micron-size dye-labeled polystyrene particles by two stage dispersion polymerization, Polymer, 47, 817-825 (2005).
Kricheldorf Hans R., Kreiser-Saunders and Caroline Boettcher, Polylactones: 31. Sn(II)octoate-initiated polymerization of L-lactide: a mechanistic study, Polymer, 36(6), 1253-59 (1995).

(Continued)

Primary Examiner — Layla Bland
(74) Attorney, Agent, or Firm — Fitch, Even, Tabin & Flannery, LLP

(57) ABSTRACT

The present invention is directed to a crosslinked or non-crosslinked polymer particle, wherein the crosslinked polymer particle comprises a copolymer of poly(alklyene glycol-graft-lactate) that is crosslinked by at least one hydrolysable monmer. Another embodiment of the present invention is a polymer particle comprising a crosslinked polymer particle that is a product of starting materials comprising (a) a hydrophilic monomer, (b) a hydrophobic monomer, and (c) a hydrolysable crosslinking agent. Another embodiment of the present invention is a polymer particle comprising, a crosslinked copolymer comprises structures represented by Formulas (I), (II), and (III), where Formulas (I), (II) and (III) are defined in the specification. Yet other embodiments of the present invention include a method of preparing a methacrylate terminated macromonomer, a method of preparing a crosslinking agent, and a method of preparing a therapeutic agent loaded nanosphere by dispersion polymerization.

36 Claims, 13 Drawing Sheets
(2 of 13 Drawing Sheet(s) Filed in Color)

(56) References Cited

OTHER PUBLICATIONS

Akala Emmanuel O., Pavla Kopeckova, Jindrich Kopecek, Novel pH-sensitive hydrogels with adjustable swelling kinetics; Biomaterials, 19, 1037-47 (1998).

Al-Ghananeem Abeer M., Malkawi Ahmad H., Muammer Yahya, Balko Justin M., Black Esther P., Mourad Walid and Romond Edward, Intratumoral Delivery of Paclitaxel in Solid Tumor from Biodegradable Hyaluronan Nanoparticle Formulations, AAPS Pharm. Sci. Tech., 10(2), 410-417 (2009).

Athanasiou Kyriacos A., C. Mauli Agrawal, F. Alan Barber and Stephen S. Burkhart, Orthopaedic applications for PLA-PGA biodegradable polymers, The Journal of Arthroscopy and Related Surgery, 14(7), 726-737 (1998).

Cadee J. A, M. De Kerf, C. J. De Groot, W. Den Otter, W. E. Hennink, Synthesis, characterization of 2-(mathacryloyloxy)-(di-) L-lactate and their application in dextran-based hydrogels, Polymer, 40, 6877-81 (1999).

Capek Ignac, Surface active properties of polyoxyethylene macromonomers and their role in radical polymerization in disperse systems, Advances in Colloid and Interface Science, 88(3), 295-357 (2000).

Eguiburu Jose Luis, Maria Fernandez Berridi and Julio San Roman, Functionalization of poly(L-lactide) macromonomers by ring-opening polymerization of L-lactide initiated with hydroxyethyl methacrylate-aluminium alkoxides, Polymer, 36(1), 173-179 (1995).

Chavanpatil Mahesh D., Patil Yogesh and Panyam Jayanth, Susceptibility of nanoparticle-encapsulated paclitaxel to P-glycoprotein-mediated drug efflux, International Journal of Pharmaceutics, 320, 150-156 (2006).

Czelusniak Izabela, Ezat Khosravi, Alan M. Kenwright, Christopher W. G. Ansell, Synthesis, Characterization, and Hydrolytic Degradation of Polylactide-Functionalized Polyoxanorbornenes, Macromolecules, 40, 1444-52 (2007).

Couvreur Patrick and Christine Vauthier, Nanotechnology: Intelligent design to treat complex disease, Pharmaceutical Research, 23(7), 1417-50 (2006).

Allemann Eric, Eric Doelker and Robert Gurny, Drug loaded Poly(lactic acid) nanoparticles produced by a reversible salting out process: Purification of an injectable dosage form, European Journal of Pharmaceutics and Biopharmaceutics, 39(1), 13-18 (1993).

Layre A., P. Couvreur, H. Chacun, J. Richard, C. Passirani, D. Requier, J. P. Benoit, R. Gref, Novel composite core-shell nanoparticles as busulfan carriers, Journal of Controlled Release, 111, 271-80 (2006).

Metters A. T., K. S. Anseth, C. N. Bowman, Fundamental studies of a novel, biodegradable PEG-b-PLA hydrogel, Polymer, 41, 3993-4004 (2000).

Iojoiu Christina, David Cade, Hatem Fessi and Thierry Hamaide, Synthesis of oligocaprolactone vinyl ether macromonomers and their use for indomethacin encapsulation in polymer nanoparticles based on polycaprolactone macromonomer-maleic anhydride-N-vinyl pyrrolidone terpolymers, Polymer International, 55, 222-28 (2006).

Jin Cheng, Bai Ling, Wu Hong, Song Wenjie, Guo Guohen and Dou Kefeng, Cytotoxicity of Paclitaxel Incorporated in PLGA Nanoparticles on Hypoxic Human Tumor Cells, Pharmaceutical Research, 26(7), 1776-1784 (2009).

Kawaguchi Seigou and Koichi Ito, Dispersion Polymerization, Advances in Polymer Science, 175, 299-328 (2005).

Kim Jin-Woong, Chung-Hyuk Lee, Jung Bae Jun, Kyung-Do Suh, Monodisperse micron-sized crosslinked polystyrene particles: VII. Importance of monomer-diffusible surface characteristics of growing particles, Colloids and Surfaces A: Physicochemical and Engineering Aspects, 194, 57-64 (2001).

Kim, Mi Sun, Gyu Ho Lee, Jae-Min Hong, Hyunjung Lee, Synthesis of Monodisperse PS-co-PDMS Microspheres by Dispersion Polymerization, Materials Science and Engineering C, 27, 1247-51 (2007).

Kunzmann Andrea, Andersson Britta, Thurnherr Tina, Krug Harald, Scheynius Annika, Fadeel Bengt, Toxicology of engineered nanomaterials: Focus on biocompatibility, biodistribution and biodegradation, Biochimica et Biophysica Acta, 1810:361-373, (2011). (e-published ahead of printing: (May 8, 2010).

Ulbrich K., V. Subr, L. W. Seymour, R. Duncan, Novel biodegradable hydrogels prepared using the divinylic crosslinking agent N,O-dimethacryloylhydroxylamine: 1. Synthesis and characterization of rates of gel degradation and rate of release of model drugs, in vitro and in vivo, Journal of Controlled Release, 24, 181-90 (1993).

Kim So Yeon, I L Gyun Shin, Young Moo Lee, Chong Su Cho, Yong Kiel Sung, Methoxy poly(ethylene glycol) and .epsilon.-caprolactone amphiphilic block copolymeric micelle containing indomethacin. II. Micelle formation and drug release behaviours, Journal of Controlled Release, 51, 13-22 (1998).

Langer Robert, Polymer-Controlled Drug Delivery Systems, Accounts of Chemical Research, 26(10), 537-42 (1993).

Soppimath Kumaresh S., Tejraj M. Aminabhavi, Anandrao R. Kulkarni, Walter E. Rudzinski, Biodegradable polymeric nanoparticles as drug delivery devices, Journal of Controlled Release, 70, 1-20 (2001).

Leobandung William, Hideki Ichikawa, Yoshinobu Fukumori, Nicholas A. Peppas, Monodisperse Nanoparticles of Poly (ethylene glycol) Macromers and N-Isopropyl Acrylamide for Biomedical Applications. Journal of Applied Polymer Science, 87, 1678-84 (2003).

Ulbrich K., V. Subr, P. Podperova, M. Buresova, Synthesis of novel hydrolytically degradable hydrogels for controlled drug release, Journal of Controlled Release, 34, 155-65 (1995).

Luo Weijun, Suming Li, Jianzhong Bei, Shenguo Wang, Synthesis and Characterization of Poly(L-lactide)-Poly (ethylene glycol) Multiblock Copolymers, Journal of Applied Polymer Science, 84, 1729-36 (2002).

Ranade Vasant V., Drug delivery systems: 3B. Role of Polymers in Drug Delivery, The Journal of Clinical Pharmacology, 30, 107-120 (1990).

Sahoo Sanjeeb K. and Labhasetwar Vinod, Enhanced Antiproliferative Activity of Transferrin-Conjugated Paclitaxel-Loaded Nanoparticles is Mediated via Sustained Intracellular Drug Retention, Molecular Pharmaceutics, 2(5), 373-383 (2005).

Sairam Malladi, V. Ramesh Babu, Boya Vijaya Kumar Naidu, Tejraj M. Aminabhavi, Encapsulation efficiency and controlled release characteristics of crosslinked polyacrylamide particles, International Journal of Pharmaceutics, 320, 131-136 (2006).

Sarac A. S., Redox Polymerization, Progress in Polymer Science, 24, 1149-1204 (1999).

Vazquez Blanca, Belen Levenfeld, Julio San Roman, Role of amine activators on the curing parameters, properties and tocixity of acrylic bone cements, Polymer International, 46, 241-50 (1998).

Wood David A., Biodegradable drug delivery systems, International Journal of Pharmaceutics, 7, 1-18 (1980).

Yang Tao, Fu-De Cui, Min-Koo Choi, Hongxia Lin, Suk-Jae Chung, Chang-Koo Shim, Dae-Duk Kim, Liposome Formulation of Paclitaxel with Enhanced Solubility and Stability, Drug Delivery, 14(5), 301-08 (2007).

Torchilin Vladimir, Multifunctional Nanocarriers, Advanced Drug Delivery Reviews, 58, 1532-1555 (2006).

Xu Peisheng, Edward A. Van Kirk, Shiyan Li, William J. Murdoch, Jun Ren, Muhammad Delwar Hussain, Maciej Radosz, Youquing Shen, Highly stable core-surface-crosslinked nanoparticles as cisplatin carriers for cancer chemotherapy, Colloids and Surfaces B: Biointerfaces, 48, 50-57 (2006).

Yin Wusheng, Emmanuel O. Akala, Robert E. Taylor, Design of naltrexone-loaded hydrolyzable crosslinked nanoparticles, International Journal of Pharmaceutics, 244, 9-19 (2002).

Ofir R, Seidman R, Rabinski T, Krup M, Yavelsky V, Weinstein Y and Wolfson M, Taxol-induced apoptosis un human SKOV3 ovarian and MCF7 breast carcinoma cells is caspase-3 and caspase-9 independent, Cell Death and Differentiation, 9, 636-642 (2002).

Zhao Yue, Jie Fu, Dennis K. P. Ng, Chi Wu, Formation and Degradation of Poly(D,L-lactide) Nanoparticles and Their Potential Application as Controllable Releasing Devices, Macromolecular Bioscience, 4, 901-06 (2004).

(56) References Cited

OTHER PUBLICATIONS

Odian George, Principles of Polymerization Second ed.; Wiley-Interscience: New York, U.S.A., pp. 194-204; 216-219; 271-275 (1981).

Huang Samuel J. and John M. Onyari, Multicomponent polymers of poly(lactic acid) macromonomers with methacrylate terminal and copolymers of poly(2-hydroxyethyl methacrylate), Journal of Macromolecular Science—Pure and Applied Chemistry A, 33(5), 571-84 (1996).

Akala Emmanuel O, Oluchi Elekwachi, Vantoria Chase, Hausalynn Johnson, Marjorie Lazarre, Kenneth Scott, Organic redox-initiated polymerization process for the fabrication of hydrogels for colon-specific drug delivery, Drug Development and Industrial Pharmacy, 29(4), 375-386 (2003).

Gerhardt Warren W., David E. Noga, Kenneth I. Hardcastle, Andres J. Garcia, David M. Collard, Marcus Weck, Functional Lactide Monomers: Methodology and Polymerization, Biomacromolecules, 7, 17-1742 (2006).

Achilias Dimitris S, and Irini D. Sideridou, Kinetics of the benzoyl peroxide/amine initiated free-radical polymerization of dental dimethacrylate monomers: Experimental studies and mathematical modeling for TEGDMA and bis-EMA, Macromolecules, 37, 4254-65 (2004).

Ober Christopher K. and Kar P. Lok, Formation of large monodisperse copolymer particles by dispersion polymerization, Macromolecules, 20, 268-273 (1987).

Ryner Maria, Anna Finne, Ann-Christine Albertsson, Hans R. Kricheldorf, L-lactide Macromonomer Synthesis Initiated by New Cyclic Tin Alkoxides Functionalized for Brushlike Structures, Macromolecules, 34, 7281-7287 (2001).

Boffa Lisa S, and Bruce M. Novak, Link-Functionalized Polymers: An unusual macromolecular architecture through bifunctional initiation, Macromolecules, 30, 3494-3506 (1997).

Sawhney Amarpreet S., Chandrashekhar P. Pathak and Jeffrey A. Hubbell, Bioerodible hydrogels based on photopolymerized poly(ethyleneglycol)-co-poly(.alpha.-hydroxy acid) diacrylate macromers, Macromolecules, 26:581-587 (1993).

CellTiter.RTM.-Glo Luminescent Cell Viability Assay Technical Bulletin, TB 288, Jun. 2009, Promega Corporation, WI, USA.

PCT Search Report and Written Opinion: PCT/US2011/061902, mailed Jul. 30, 2012, which corresponds to U.S. Appl. No. 12/952,843 (9 pages).

PCT Search Report and Written Opinion: PCT/US2011/061917, mailed Jul. 20, 2012, which corresponds to U.S. Appl. No. 12/952,856 (10 pages).

Shenoy, D. B., Amiji, M. M., Poly(ethylene oxide)-modified poly(-caprolactone) Nanoparticles for Targeted Delivery of Tamoxifen in Breast Cancer, Int. J. Pharm., 293, 261-70 (2005).

Cammas, S., Suzuki, K.; Sone, C.; Sakurai, Y., Kataoka, K., Okano, T, Thermo-Responsive polymer nanoparticles with a Core-Shell Micelle Structure as Site-Specific Drug Carriers, Journal of Controlled Release 48, 157-64 (1997).

Yokoyama, M., Okano, T., Targetable Drug Carriers: Present Status and a Future Perspective, Advanced Drug Delivery Reviews 21, 77-80 (1996).

Kawaguchi, S., Winnik, M. A., Ito, K., Dispersion Copolymerization of n-Butyl Methacrylate with Poly(ethylene oxide) Macromonomers in Methanol-Water: Comparison of Experiment with Theory, Macromolecules 28, 1159-66 (1995).

Robinson, D. N., Peppas, N. A., Preparation and Characterization of pH-Responsive Poly(methacrylic acid-g-ethylene glycol) nanospheres, Macromolecules 35, 3668-74 (2002).

Huang, S. K., Stauffer, P. R., Hong, K., Uuo, J. W. H., Philips, T. L., Huang, A., Papahadjopoulos, D., Liposomes and Hyperthermia in Mice: Increased Tumor Uptake and Therapeutic Efficacy of Doxorubicin in Sterically Stabilized Liposomes, Cancer Research 54, 2186-91 (1994).

Bakare, O., Ashendel, C. L., Peng, H., Zalkow, L. H., Burgess, E. M., Synthesis of MEK1 Inhibitory Activities of Imido-Substituted 2-Chloro-1,4-naphthoquinones, Bioorganic & Medicinal Chemistry 11, 3165-70 (2003).

Yin, W., Akala, E. O., Taylor, R. E., Design of Naltrexone-Loaded Crosslinked Nanoparticles, International Journal of Pharmaceutics 244, 9-19 (2002).

Bamnolker, H., Margel, S., Dispersion Polymerization of Styrene in Polar Solvent: Effect of Reaction parameters on Microsphere Surface Composition and Surface Properties, Size and Size Distribution, and Molecular Weight, Journal of Polymer Science: Part A: Polymer Chemistry 34, 1857-71 (1996).

Rosier, A., Vandermeulen, W. M., Klok, H.-A., Advanced Drug Delivery Devices via Self-Assembly of Amphiphilic Block Copolymers, Advanced Drug Delivery Reviews 53, 95-108 (2001).

Feng, S.-S., Chien, S., Chemotherapeutic Engineering: Application and Further Development of Chemical Engineering Principles for Chemotherapy of Cancer and Other Diseases, Chemical Engineering Science 58, 4087-4114 (2003).

Ramtoola, Z., Corrigan, O. I, Barrett, C. J., Release Kinetics of Fluphenazine from Biodegradable Microspheres, Journal of Microencapsulation, 9, 415-23 (1992).

Pakunlu, R. I., Wang, Y., Tsao, William, Pozharov, V., Cook, T. J., Minko, T., Enhancement of the Efficacy of Chemotherapy for Lung Cancer by Simultaneous Suppression of Multidrug Resistance and Antiapoptotic Cellular Defense: Novel Multicomponent Delivery System, Cancer Research, 64, 6214-6224 (2004).

Nasongkla, Norased, Bey, Erik, Ren, Jimin, Ai, Hua, Khemtong, Chalermchai, Guthi, Jagadeesh Setti, Chin, Shook-Fong, Sheery, A. Dean, Boothman, David A. and Gao, Jinming, Multifunctional Polymeric Micelles as Cancer-Targeted, MRI-Ultasenstive Drug Delivery Systems, Nano Letters, 6(11), 2427-2430 (2006).

Ferrari, M. Cancer Nanotechnology: Opportunities and Challenges, Nature Reviews/Cancer, 5; 1-11 (2005).

Gaither, A., Lourgenko, V., RNA Interference Technologies and their Use in Cancer Research, Curr. Opin. Oncol., 19:50-54 (2007).

Lasic, D. D., Martin, F. J., Gabizon, A., Huang, S. K., Papahadjopoulos, D., Sterically Stabilized Liposomes: A Hypothesis on the Molecular Origin of the Extended Circulation Times, Biochimica et Biophysica Acta (BBA)—Biomembranes 1070, 187-92 (1991).

Burm, J.-P., Jhee, S. S., Chin, A., Moon, Y. S. K., Jeong, E., Nii, L., Fox, J. L., Gill, M. A., Stability of Paclitaxel with Ondansetron Hydrochloride or Ranitidine Hydrochloride During Simulated Y-Site Administration, American Journal of Hospital Pharmacy 51, 1201-1204 (1994).

Minko, T., Dharap, S. S., Pakunlu, R. I., Wang, Y., Molecular Targeting of Drug Delivery Systems to Cancer, Current Drug Targets, 5, 389-406 (2004).

Trail, P. A., Wilner, D., Lasch, S. J., Henderson, A. J., Hofstead, H., Casazza, A. M., Firestone, R. A., Hellstrom, K. E., Cure of Xenografted Human Carcinomas by BR96-Doxorubicin Immunoconjugates, Science 261, 212-15 (1993).

Cancer Nanotechnology (Going Small for Big Advances: Using Nanotechnology to Advance Cancer Diagnosis, Prevention and Treatment). U.S. Department of Health and Human Services, National Institutes of Health/National Cancer Institute. NIH Publication No. 04-5489, 2004).

Eric M Pridgen, Robert Langer, Omid C Farokhzad Biodegradable, polymeric nanoparticle delivery systems for cancer therapy, Nanomedicine, 2(5), 669-80 (Oct. 2007).

Longnecker, S. M., Donehower, R. C., Cates, A. E., Chen, T.-L., Brundrett, R. B., Grochow, L. B., Ettinger, D. S., Colvin, M., High-Performance Liquid Chromatography Assay for Taxol in Human Plasma and Urine and Pharmacokinetics in a Phase I Trial, Cancer Treatment Reports 71, 53-59 (1987).

Nugroho, M. B., Kawaguchi, S., Ito, K., Winnik, M. A, Control of Particle Size in Dispersion Polymerization Using Poly (ethylene oxide) Macromonomers, Macromolecular Reports A32, 593-601 (1995).

(56) References Cited

OTHER PUBLICATIONS

Sant, S et al., Effect of polymer architecture on surface properties, plasma protein adsorption, and cellular interactions of pegylated nanoparticles, Journal Biomedical Materials Research Part 87A(4): 885-895 (2008).

Scheler, S et al., Cellular uptake and degradation behavior of biodegradable poly(ethylene glycol-graft-methyl methacrylate) nanoparticles crosslinked with dimethacryloyl hydroxylamine, International Journal Pharmaceutical 103, 207-218 (2011) (available online Oct. 2010).

Yin, W et al., Design of naltrexone-loaded hydrolyzable crosslinked nanoparticles, International Journal Pharmaceutical 244, 9-19 (2002).

Daniel Horak et al., Poly(2-hydroxyethyl methacrylate)-based slabs as a mouse embryonic stem cell support, Biomaterials 25 (2004) 5249-5260.

European Patent Office Extended European Search Report dated May 21, 2014 for European Application No. 11842912.5, 6 pages.

* cited by examiner

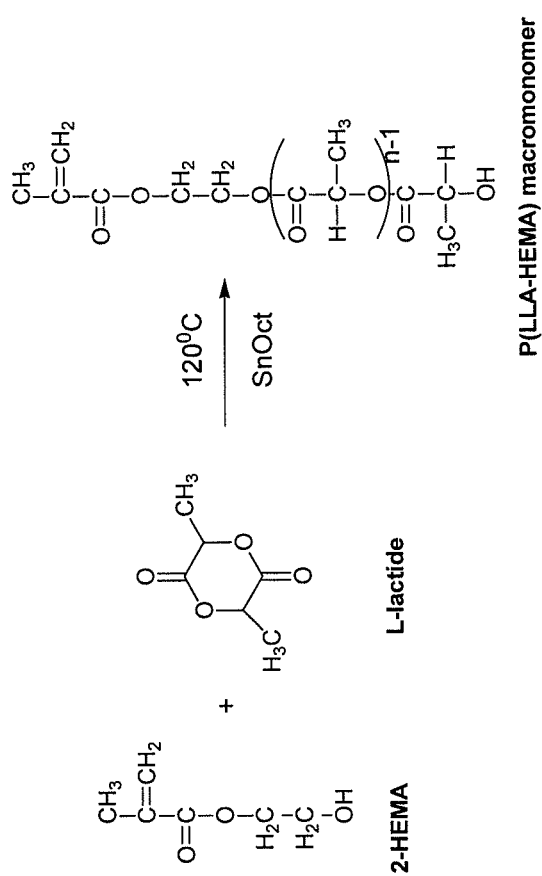
Figure 1-A

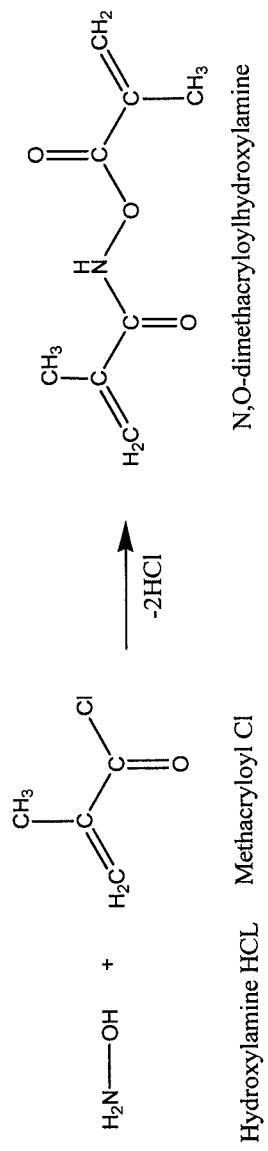
Figure 1-B

BIODEGRADABLE STEALTH POLYMERIC PARTICLES FABRICATED USING THE MACROMONOMER APPROACH BY FREE RADICAL DISPERSION POLYMERIZATION

STATEMENT REGARDING FEDERALLY SPONSORED RESEARCH OR DEVELOPMENT

This invention was made with government support under NIH Research Grant NIH CA138179 awarded by the National Institutes of Health. The government has certain rights in the invention.

TECHNICAL FIELD

The present invention relates to the production and use of polymer particles, which may be used to deliver therapeutic agents, wherein the polymer particles are fabricated using a macromonomer approach by free radical polymerization. The introduction of a double bond in the hydrophobic PLA macromonomer for the fabrication of the particle greatly increases its versatility and yields macromonomers capable of further polymerization. These end-capped macromonomers offer an approach to synthesize novel resorbable copolymers with "tailored" properties.

BACKGROUND

One of the great challenges in medicine is finding more effective forms of treatment for a large number of life-threatening diseases such as cancer. One of the challenges to be overcome relates to the inadequacies surrounding the ability to administer therapeutic agents so that the therapeutic agents selectively reach the desired targets without damaging healthy cells or being blocked by biological barriers. Thus, to increase efficiency per dose of a therapeutic agent, efforts need to be made in the direction of increasing therapeutic agent delivery, including circumventing the biological barriers that prevent a therapeutic agent from reaching its target.

Of particular interest is the development of drug delivery systems based on nanotechnology that can achieve both targeting (spatial/distribution control) and controlled release (temporal control) of drugs or therapeutic agents. This is because it is believed that if spatial targeting is combined with temporal release, an improved therapeutic index may be obtained. For example, if drug release or activation is made locally at the therapeutic site or biophase, then selectivity will be increased by a multiplication of the spatial selectivity times the advantage of local drug release/activation. Further, the therapeutic index may be improved by a combination of spatially selected delivery and a preferable pattern of release for the therapeutic agent over long time periods or using a pulsatile release, which would be preferable for certain pharmacological activities of the therapeutic agents used in, for example, chronotherapeutics.

SUMMARY

Generally, two main approaches have been used for the preparation of biodegradable polymers. These include the modification of known biodegradable polymers and the design of new polymers with degradable potential. The polyesters are the most widely used polymers in this class because of their biocompatibility and non-immunogenic and non-toxic characteristics. These are esters of α-hydroxy acids, including, but not limited to, poly (lactic acid) (PLA), poly (glycolic acid) (PGA), polycaprolactone (PCL), and their copolymers such as poly (lactide)-co-(glycolide) (PLGA). The observation that a crosslinked system is possible with functionalized poly (lactic acid) (PLA) makes the design of a novel biodegradable polymeric PLA-based system possible, the characteristics of which are amenable to control. Thus, the functionalization of PLA by the introduction of a double bond would greatly increase its versatility and yield macromonomers capable of further polymerization. These end-capped macromonomers offer an approach to synthesize novel resorbable copolymers with "tailored" properties. Furthermore, crosslinked networks to control drug release and degradation rate can be introduced.

One embodiment of the present invention relates to the preparation of crosslinked and non-crosslinked polyethylene glycol-polylactide (PEG-PLA) or polycaprolactone (PEG-PCL) polymer particles (nanoparticles) by free radical dispersion polymerization. Furthermore, the present disclosure relates to attaching a targeted moiety to the PEG coating which distinguishes it from the widely used method of nanoparticle preparation using preformed polymers. Thus, a therapeutic agent may be more effectively delivered to a target while minimizing adverse side effects.

Another embodiment of the present invention relates to a polymer particle and methods of production and use thereof. The polymer particle may include a group capable of avoiding biological recognition (biofouling), a group capable of being cleaved into two or more separate groups, and a group capable of being further modified by a secondary chemical reaction. The polymer particle may also contain a therapeutic agent.

More specifically, the present invention relates to:

A crosslinked or non-crosslinked polymer particle which comprises a copolymer of poly(alklyene glycol-graft-lactate) that is optionally crosslinked by at least one hydrolysable monomer.

A polymer particle wherein the copolymer is poly(ethylene glycol-graft-P (LLA-HEMA) macromonomer)).

A polymer particle wherein the hydrolysable crosslinker is N.O-dimethacryolhydroxylamine.

A polymer particle wherein a ratio of alkene glycol to lactate is from about 0.25:1 to about 5:1.

A polymer particle wherein the amount of hydrolysable group is from about 0 mol % (for non-crosslinked particles) to about 10 mol % based on the total amount of copolymer.

A polymer particle wherein the average size is from about 50 nm to about 700.5 nm.

A polymer particle having a polydispersity from about 0.0103 to about 0.507.

A polymer particle further comprising a therapeutic agent.

A polymer particle further comprising a therapeutic agent selected from the paclitaxel or docetaxel or any other suitable therapeutic agent.

A crosslinked polymer particle comprising: (a) a hydrophobic monomer, (b) a hydrophilic monomer, and (c) a hydrolysable crosslinking agent.

A polymer particle wherein the hydrophilic monomer is an alkene glycol acrylate.

A polymer particle wherein the hydrophilic monomer is a poly(ethylene glycol) monomethyl ether mono methacrylate.

A polymer particle wherein the hydrophobic monomer is P (LLA-HEMA) macromonomer.

A polymer particle wherein the hydrolysable crosslinking agent is N,O-dimethylacryloylhydroxylamine.

A polymer particle wherein a ratio of the hydrophilic monomer to the hydrophobic monomer is from about 0.25:1 to about 5:1.

A polymer particle wherein the amount of hydrolysable group is from about 0 mol % (for non-crosslinked nanoparticles) to about 10 mol % based on the total amount of the first hydrophilic monomer and the second hydrophilic monomer.

A polymer particle wherein the average size is from about 50 nm to about 700.5 nm.

A polymer particle wherein a polydispersity is from about 0.0103 to about 0.507.

A polymer particle further comprising a therapeutic agent, targeting moieties and or imaging contrast agents.

In another embodiment, the present invention is a polymer particle further comprising a therapeutic agent selected from the group consisting of paclitaxel, and docetaxel.

A a crosslinked or non-crosslinked polymer particle, which comprises a copolymer comprising structures represented by Formulas (I), (II), and optionally (III):

$$-(CH_2-\underset{\underset{CO}{|}}{\overset{\overset{R_2}{|}}{C}})_x-$$
$$\underset{\underset{O}{|}}{\overset{}{|}}$$
$$(CH_2)_m$$
$$O$$
$$\begin{matrix} O= & \\ H & -CH_3 \\ & O \\ & (p-1) \\ O= & \\ H_3C & -H \\ & OR_1 \end{matrix}$$

Formula (II)

$$-(CH_2-\underset{\underset{CO}{|}}{\overset{\overset{R_3}{|}}{C}})_y-$$
$$O$$
$$CH_2$$
$$CH_2$$
$$(O)_n$$
$$R_4$$

Formula (III)

$$-(CH_2-\underset{\underset{CO}{|}}{\overset{\overset{R_5}{|}}{C}})_z-,$$
$$A_1$$
$$A_2$$
$$R_6$$

wherein $R_2$-$R_5$ each represent a group, which may be the same or different from each other, and the group is selected from the group consisting of a hydrogen, a halogen, an alkyl group having one to five carbon atoms, wherein $R_1$ represents a group that is selected from the group consisting of hydrogen, a halogen, and an alkyl group having one to 20 twenty carbon atoms, wherein $R_6$ represents another chain of the crosslinked polymer that is comprised of the structures represented by Formulas (I), (II), and (III), wherein x, y, and z represent an integer from 1 to 100, wherein n represents an integer 1 to 10,000, wherein $A_1$ is an oxygen atom or a secondary amine, where $A_2$ is an oxygen atom or a secondary amine, wherein m is an integer between 1-10, wherein p is an integer 1 to 10,000. Formula (III) is not present in the non-crosslinked polymer.

A polymer particle wherein $R_2$-$R_5$ each represent a methyl group and $R_1$ represents a hydrogen atom.

A polymer particle comprising a noncrosslinked polymer particle which comprises structures represented by Formula (I) and (II) above.

A polymer particle wherein a ratio of the structure represented by Formula (I) to Formula (II) is from about 1:0.25 to about 1:5.

A polymer particle wherein the amount of Formula (I) relative to the amount of the sum of Formulas (I) and (II) is from about 0.2 mol % to about 1 mol % based on the total amount of copolymer.

In another embodiment, the present invention is a method of preparing a methacrylate terminated macromonomer, the method comprising the steps of:

(i) reacting L-lactide, an initiator and a catalyst under vacuum for 10 minutes (ii) flushing the reaction vessel with nitrogen for 24-38 hours at a temperature of 80-160° C.

(iii) extracting the resulting polymer from an organic solution.

A method of preparing a methacrylate terminated macromonomer, wherein the initiator is selected from the group consisting of hydroxymethacrylate (HEMA) and hydroxypropylmethacrylamide (HPMA).

A method of preparing a methacrylate terminated macromonomer, wherein the initiator is HEMA.

A method of preparing a methacrylate terminated macromonomer, wherein the catalyst is selected from the group consisting of aluminium alkoxides, tin alkoxides, and stannous octoate A method of preparing a methacrylate terminated macromonomer, wherein the catalyst is stannous octoate.

A method of preparing a methacrylate terminated macromonomer, wherein the organic solvent is chloroform.

A method of preparing a methacrylate terminated macromonomer, wherein the amount of L-lactide is 0.0418 moles.

A method preparing a methacrylate terminated macromonomer, wherein the amount of initiator is 0.00738 mole.

A method of preparing a crosslinking agent, the method comprising the steps of:

(i) dissolving a reagent that supplies a hydroxamic acid moiety in a basic solvent;

(ii) adding an organic solution containing a compound having a polymerizable functional group to the solution of step (i);

(iii) stirring the reaction mixture under room temperature for 40 minutes, followed by stirring at room temperature for greater than one hour; and, (iv) extracting the resulting compound from the reaction mixture.

A method of preparing a crosslinking agent, wherein the reagent that supplies the hydroxamic acid moiety is hydroxylamine hydrochloride.

A method of preparing a crosslinking agent, wherein the compound having a polymerizable functional group is methacryloyl chloride.

A method of preparing a crosslinking agent, wherein the amount of hydroxylamine hydrochloride is 0.036 moles.

A method of preparing a crosslinking agent, wherein the basic solvent is pyridine.

A method of preparing a crosslinking agent, wherein the amount of basic solvent is 0.3298 moles.

A method of preparing a crosslinking agent, wherein the amount of methacryloyl chloride is 0.085 moles.

A method of preparing a crosslinking agent, wherein the organic solvent is chloroform.

A method of preparing a therapeutic agent loaded nanosphere by dispersion polymerization, wherein the method comprises the steps of:

(i) reacting a hydrophilic macromonomer and a hydrophobic macromonomer, with or without a crosslinker in an organic solvent/water solvent system;

(ii) adding N-phenyldiethanolamine (NPDEA) and benzoyl peroxide (BPO) at predetermined intervals to the reaction mixture of step (i) under a nitrogen atmosphere;

(iii) dissolving the therapeutic agent in an organic phase containing the hydrophobic monomers; and, (iv) recovering the therapeutic agent loaded nanospheres.

A method of preparing a therapeutic agent loaded nanosphere by dispersion polymerization, wherein the therapeutic agent is paclitaxel or any other therapeutic agent.

A method of preparing a therapeutic agent loaded nanosphere by dispersion polymerization, wherein the first and second macromoners are selected from the group consisting of polyglycolide (PGA) macromonomer, polylactide (PLA) macromonomer, polycaprolactone (PCL) macromonomer, poly(lactide-co-glycolide) (PLGA) macromonomer, poly(propylene fumarate) PFF, methacryloyl-teiminated PMMA macromonomer, methacrylate-teiminated/functionalized poly(dimethylsiloxane) macromonomer (PDMS-MA), methacryloylpolystyrene (MA-Pst) (i.e styrene macromonomers with methacryloyl end group), (vinylbenzyl)polystyrene (VB-Pst) (i.e styrene macromonomers with a vinylbenzyl end group), 2-oxyethylmethacrylate-terminated PLLA macromonomer (MC), vinylbenzyl-terminated polyisoprene (PI) macromonomers, poly(ethylene glycol)-co-poly(A-hydroxyacid) diacrylate macromers, oligocaprolactone vinyl ether macromonomer, PEG-PLA macromer, PEG-PLA-PEG macromer, poly(ethylene oxide) (PEO) block functionalized with styryl, methacryloyl, thiol, maleate, vinyl, p-vinylphenylalkyl reactive end groups, methacryloxypropyl- and vinyl-terminal polysiloxanes, α-methacryloylpoly(E-caprolactone) (PCL) macromonomer, poly(glycolide) macromonomers, HEMA terminated oligo(L-lactide) or oligo(D-lactide) macromonomers, oligoNIPAAm (oligo N-isopropylacrylamide) and polyNIPAAm (poly(N-isopropylacrylamide)) macromonomers, poly(n-butylacrylate) macromonomers, n-butyl acrylate, methyl acrylate (MA), methyl methacrylate(MMA), N,N'-dimethyl acrylamide (DMA); N-vinyl pyrrolidone (VP), hydroxyethyl methacrylate, n-butyl methacrylate, acrylamide, hydrophilic N-(2-hydroxypropylmethacrylamide) (HPMA), methyl-, ethyl-butyl-, octylcyanoacrylates (anionic polymerization) to form poly(alkylcyanoacrylates)(PACA) (biodegradable, pH sensitive), acrylic acid, 2-hydroxypropyl methacrylate (HPMA), N,N-dimethylaminoethyl methacrylate (DMAEMA), hydrophilic polymers or macromonomers, poly(vinyl pyrrolidone), (hydroxypropyl) cellulose (HPC), poly(acrylic acid), poly [N-(2-hydroxypropyl)methacrylamide] (PHMPA), dextrans, e.g. dextran-10, -40, -70, poloxamer-188, -184, -237, polyethylene glycol (PEG), polyethylene oxide (PEO) and PEO macromonomers with p-vinylbenzyl and methacrylate end groups, poloxamine, polysorbates, methacryloyl-terminated poly(ethylene oxide) macromonomer, poly(2-alkyl-2-oxazolin), poly(methacrylic acid), poly(acrylic acid) macromonomers, bifunctional vinyl urethane macromonomers, vinyl terminus polysiloxane macromonomer, poly(vinyl alcohol), polyacrylamide, and poly(glutaraldehyde).

A method of preparing a therapeutic agent loaded nanosphere by dispersion polymerization, wherein the hydrophobic macromonomer is P (LLA-HEMA) macromonomer A method of preparing a therapeutic agent loaded nanosphere by dispersion polymerization, wherein the hydrophilic macromonomer is polyethylene glycol-monomethylether monomethylmethacrylate.

A polymer particle, wherein an encapsulation efficiency (EE) is calculated from the following formula:

$$EE = \frac{(A_{prep}) - (A_{wash}) \times 100\%}{(A_{prep})},$$

wherein $A_{prep}$ is an amount of therapeutic agent used in nanosphere preparation, and $A_{wash}$ is an amount of the therapeutic agent remaining at the end of preparation of the therapeutic agent loaded nanosphere.

A polymer particle, wherein the encapsulation efficiency is 31.9%.

A polymer particle, wherein a drug loading (DL) is calculated from the following formula:

$$DL = \frac{(A_{PIS}) \times 100\%}{(A_{NP})},$$

where $A_{PIS}$ is an amount of therapeutic agent dissolved in solution, and $A_{NP}$ is an amount of therapeutic agent dissolved in acetonitrile.

A polymer particle, wherein the drug loading is 0.25%-5% w/w.

Examples of the macromonomers may preferably include, but are not limited to, polyglycolide (PGA) macromonomer, polylactide (PLA) macromonomer, polycaprolactone (PCL) macromonomer, poly(lactide-co-glycolide) (PLGA) macromonomer, poly(propylene fumarate) PFF, methacryloyl-terminated PMMA macromonomer, methacrylate-terminated/functionalized poly(dimethylsiloxane) macromonomer (PDMS-MA), methacryloylpolystyrene (MA-Pst) (i.e styrene macromonomers with methacryloyl end group), (vinylbenzyl)polystyrene (VB-Pst) (i.e styrene macromonomers with a vinylbenzyl end group), 2-oxyethylmethacrylate-terminated PLLA macromonomer (MC), vinylbenzyl-terminated polyisoprene (PI) macromonomers, poly(ethylene glycol)-co-poly(a-hydroxyacid) diacrylate macromers, oligocaprolactone vinyl ether macromonomer, PEG-PLA macromer, PEG-PLA-PEG macromer, poly(ethylene oxide) (PEO) block functionalized with styryl, methacryloyl, thiol, maleate, vinyl, p-vinylphenylalkyl reactive end groups, methacryloxypropyl- and vinyl-terminal polysiloxanes, α methacryloylpoly(E-caprolactone) (PCL) macromonomer, poly(glycolide) macromonomers, HEMA terminated oligo(L-lactide) or oligo(D-lactide) macromonomers, oligoNIPAAm (oligo N-isopropylacrylamide) and polyNIPAAm (poly(N-isopropylacrylamide)) macromonomers, poly(n-butylacrylate) macromonomers, n-butyl acrylate, methyl acrylate (MA), methyl methacrylate(MMA), N,N'-dimethyl acrylamide (DMA); N-vinyl pyrrolidone (VP), hydroxyethyl methacrylate, n-butyl methacrylate, acrylamide, hydrophilic N-(2-hydroxypropylmethacrylamide) (HPMA), methyl-, ethyl-butyl-, octylcyanoacrylates (anionic polymerization) to form poly(alkylcyanoacrylates) (PACA) (biodegradable, pH sensitive), acrylic acid, 2-hydroxypropyl methacrylate (HPMA), N,N-dimethylaminoethyl methacrylate (DMAEMA) and hydrophilic polymers or macromonomers.

Further examples of the macromonomers may preferably include, but are not limited to, poly(vinyl pyrrolidone) macromonomer, (hydroxypropyl) cellulose (HPC) macromonomer, poly(acrylic acid) macromonomer, poly[N-(2-hydroxypropyl)methacrylamide] (PHMPA) macromonomer, dextrans, e.g., dextran-10, -40, -70, poloxamer-188, -184, -237, polyethylene glycol (PEG), polyethylene oxide (PEO) and PEO macromonomers with p-vinylbenzyl and methacrylate end groups, poloxamine, polysorbates, methacryloyl-terminated poly(ethylene oxide) macromonomer, poly(2-alkyl-2-oxazolin), poly(methacrylic acid), poly(acrylic acid) macromonomers, bifunctional vinyl urethane macromonomers, vinyl terminus polysiloxane macromonomer, poly(vinyl alcohol), polyacrylamide, and poly(glutaraldehyde).

The group capable of avoiding biological recognition is not generally limited, so long as the group has the function of preventing proteins and biological molecules from binding the surface of the polymer particle. The group capable of avoiding biological recognition may preferably be a group that is hydrophilic and charge neutral. Examples of a group capable of avoiding biological recognition may include, but are not limited to, homo polymers or copolymers of polyalkylene glycols, such as poly(ethylene glycol), poly(propylene glycol), poly(butylene glycol), and may include acrylates or acrylamides, such as hydroxyethyl methacrylate, N-(2-hydroxypropylmethacrylamide) (HPMA), and 2-hydroxypropyl methacrylate.

The group capable of being cleaved into two or more groups is not particularly limited, so long as the group is capable of being cleaved by the presence of specific environmental conditions. Examples of a group capable of being cleaved includes, but is not limited to, hydrolysable groups, biodegradable groups, heat degradable and photo degradable groups. A hydrolysable group may include a group that is capable of being cleaved by exposure to specific pH conditions.

Examples of a hydrolysable monomer may include N,O-dimethylacryloylhydroxylamine, which may be produced from starting materials such as N,O-hydroxylamine. Further, the hydrolysable group may have two or more functional groups, such as unsaturated bonds, such that the hydrolysable group may be incorporated into a crosslinking agent. By incorporating the hydrolysable group into a crosslinking agent, the crosslinking agent having the hydrolysable group may be copolymerized with another monomer to produce a crosslinked copolymer particle, wherein at least one of the crosslinking groups is hydrolysable under specific environmental conditions.

The group capable of being further modified by a secondary chemical reaction is not generally limited, but may be esters of α-hydroxy acids, such as poly (lactic acid) (PLA) macromoner, poly (glycolic acid) (PGA) macromonomer, polycaprolactone (PCL) macromonomer and their copolymers such as poly (lactide)-co-(glycolide) (PLGA).

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1-A is an illustration of the synthesis of methacrylate terminated poly(lactide) (PLA) macromonomer ($85_{LLA}$: $15_{HEMA}$).

FIG. 1-B is an illustration of the synthesis of the crosslinking agent N,O-Dimethacryloylhydroxylamine (MANHOMA).

DETAILED DESCRIPTION OF EXEMPLARY EMBODIMENTS

Figure 1:
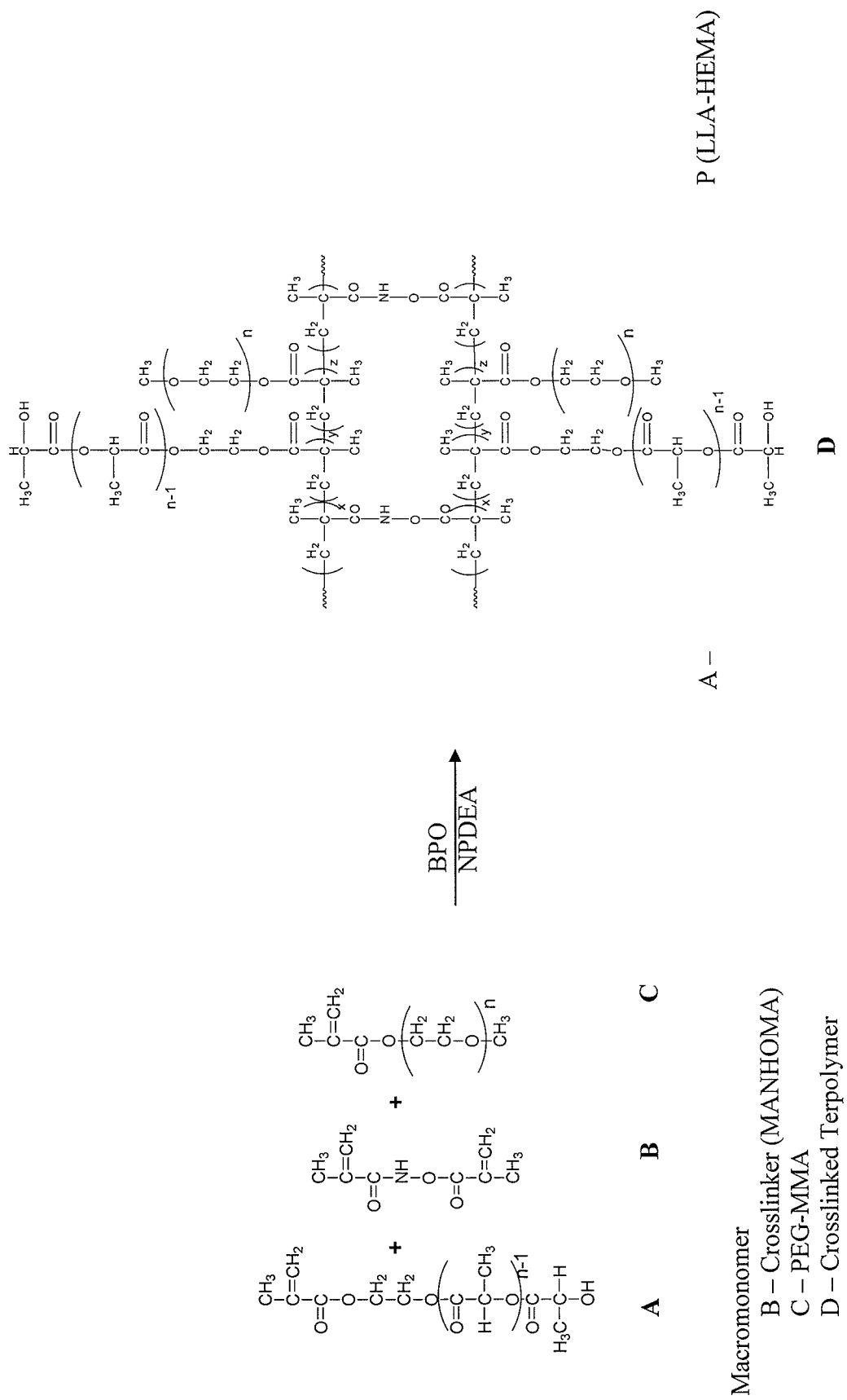
FIG. 1 is an illustration of the synthesis and structure of polyethylene-glycol covered (stealth) hydrolysable crosslinked poly(L-lactic acid-hydroxyethyl methacrylate P(LLA-HEMA) nanoparticle.

In one embodiment, a polymer particle (nanoparticle) comprises a crosslinked polymer particle, wherein the crosslinked polymer includes a copolymer of poly(alkene glycol-graft-lactide) that is crosslinked by at least one hydrolysable group. The copolymer may be poly(ethylene glycol-graft-methacrylate terminated poly(lactide) (PLA)), and the hydrolysable monomer may be N,O-dimethacryloylhydroxylamine. Further, the ratio of alkene glycol to lactide is preferably from about 0.25:1 to about 5:1, the amount of hydrolysable monomer is preferably from about 0 mol % (for the non-cross linked) to about 10 mol % based on the total amount of copolymer, and the average size of the polymer particle is preferably from about 50 nm to about 700.5 nm, and has a polydispersity of preferably from about 0.0103 to about 0.507.

In another embodiment, a polymer particle (nanoparticle) may be a crosslinked or non-crosslinked polymer particle that is a product of starting materials including (a) a hydrophilic monomer, (b) a hydrophobic monomer, and (c) a hydrolysable crosslinking agent. The hydrophilic monomer may be an alkene glycol acrylate, such as poly(ethylene glycol) monomethyl ether mono methacrylate. The hydrophobic monomer may be a poly(L-lactate) alkyloxy methyl methacrylate, such as methacrylate terminated poly(lactide) (PLA). The hydrolysable crosslinking agent may be any monomer having two unsaturated bonds and a hydrolysable group, such as N,O-dimethylacryloylhydroxylamine. In addition, the ratio of the hydrophilic monomer to the hydrophobic monomer is preferably from about 0.25:1 to about 5:1, the amount of hydrolysable monomer is preferably from about 0 mol % (fro the non-crosslinked nanoparticles) to about 10 mol % based on the total amount of the first hydrophilic monomer and the second hydrophilic monomer, and the average size of the polymer particle is preferably from about 50 nm to about 700.5 nm, and has a polydispersity of from preferably about 0.0103 to about 0.507.

In another embodiment, a crosslinked copolymer preferably comprises structures represented by Formulas (I), (II), and (III):

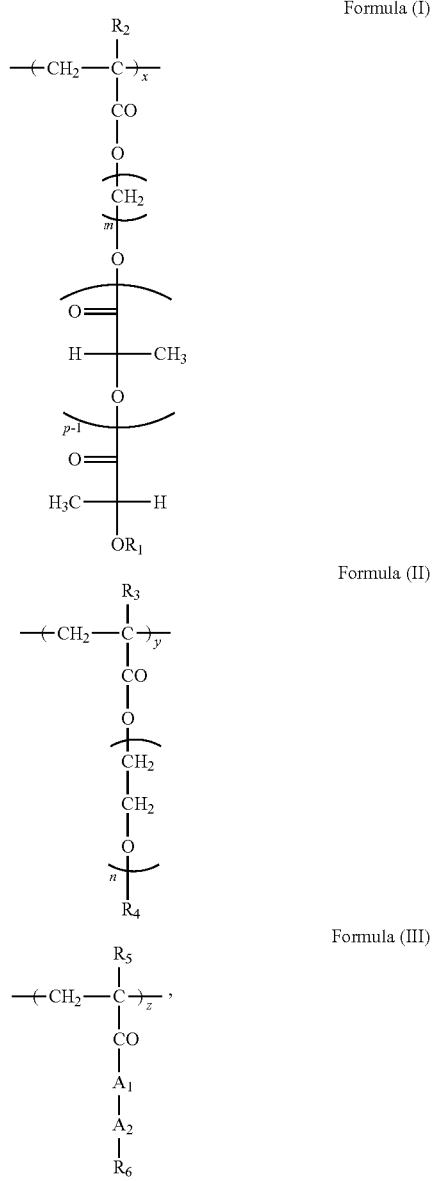

wherein $R_2$-$R_5$ each represents a group, which may be the same or different from each other, and the group is selected from the group consisting of a hydrogen, a halogen, an alkyl group having one to five carbon atoms, wherein $R_1$ represents a group that is selected from the group consisting of hydrogen, a halogen, and an alkyl group having one to twenty carbon atoms, wherein $R_6$ represents another chain of the crosslinked polymer that is comprised of the structures represented by Formulas (I), (II), and (III), wherein x, y, and z represent an integer from 1 to 100, wherein n represents an integer 1 to 10,000, wherein $A_1$ is an oxygen atom or a secondary amine, where $A_2$ is an oxygen atom or a secondary amine, wherein m is an integer between 1-10, wherein p is an integer 1 to 10,000. In addition, a ratio of the structure represented by Formula (I) to Formula (II) may preferably be from about 1:0.25 to about 1:5, the amount of Formula (I) relative to the amount of sum of Formulas (I) and (II) may preferably be from about 0.2 mol % to about 1 mol % based on the total amount of copolymer, and the average size of the polymer particle may be from about 50 nm to about 700.5 nm, and has a polydispersity of from about 0.0103 to about 0.507. Further, $R_2$-$R_5$ may each represent a methyl group and $R_1$ represents a hydrogen atom. Formula (III) is optionally present in the non-crosslinked polymer.

Examples of crosslinkers used in the preparation of the polymer particles described above include, but are not limited to, polypropylene fumarate)-diacrylate (PFF-DA) macromer, N-vinyl pyrrolidone—to fours PVP crosslinks, poly(ethylene glycol)-dimethacrylate (PEG-DMA), ethylene glycol dimethacrylate (EGDMA), 4,4'-di(methacryloylamino) azobenzene (DMAAB), N,N'-methylenebisacrylamide, hydrophilic N-isopropyl acrylamide, divinyl benzene (DVB), tetraethylene glycol dimethacrylate, ethylene glycol divinyl carbonate (EGDVC); and, methacryloxyethyl vinyl carbonate (HEMAVC).

Examples of solvents used in the preparation of the polymer particles described above include, but are not limited to, dichloromethane, water, ethanol, hexane, ethyl acetate, acetone, DMSO, THF and the like.

Examples of initiators used in the preparation of the polymer particles described above include, but are not limited to, benzoyl peroxide (BPO), azo-bis-isobutyronitrile (AIBN), potasium persulfate (KPS), 2,2'-azobis-2,4-dimethylvaleronitrile (ADVN), PDMS macroazoinitiator (PDMS-azo), ammonium persulfate, thermal 2,2'-azobis [N-(2-carboxyethyl)-2-2-methylpropionamidine](VA-057) (amphoteric pH sensitive initiator), redox initiators, and photoinitiators.

Examples of redox initiators include, but are not limited to, BPO activated by tertiary amines such as: N,N-dimethyl-4-toluidine (DMT), N,N-dimethylbenzyl methacrylate, N,N-dimethylbenzyl alcohol, N,N-dimethylaniline, 4-N,N-dialkyl aminophenalkanoic acids and their methyl esters, peroxides, persulfate, peroxomonosulfate, peroxidiphosphate, metal ion oxidant-reducing agent systems which include but are not limited to Mn(III) and Mn(VII), Ce(IV), V(V), Co(III), Cr(VI) and Fe(II and III).

Examples of photoinitiators include, but are not limited to 2,2-dimethoxy-2-phenylacetophenone, Quantacure ITX photosensitizer, Irgacure 907 (1-907) initiator systems, and N,N-dimethyl ethanol amine.

Any of the above embodiments may also include a therapeutic agent, wherein the therapeutic agent is contained or encapsulated inside the polymer particle. The polymer particle may then function as package for controlling and separately delivering the therapeutic agent until predetermined environmental conditions. For example, in one embodiment, a therapeutic agent might be incorporated into the particle during the copolymerization process. The particle polymer would then prevent the therapeutic agent from prematurely being absorbed by the body or encountering biological barriers, such as macrophages, or even being prematurely excreted as waste. When the polymer particle is exposed to the predetermined environmental conditions, the group capable of being cleaved into two or more groups would be cleaved into two or more groups to reduce crosslinking in such a way as to release the therapeutic agent from the interior of the polymer particle to the local environment. The specific nature of the predetermined environmental conditions necessary to effect release would be determined by the choice of the group capable of being cleaved into two or more groups. For example, when the group capable of being cleaved into two or more groups is a hydrolysable monomer such as N,O-dimethylacryloylhydroxylamine or a polymer particle produced from N,O-dimethylacryloylhydroxylamine, then the particle is stable at pH values below 5 and degraded at pH 6.5 and above.

The term therapeutic agent includes, but is not limited to, a pharmacologically active agent that produces a local or systemic effect in a mammal. The term thus means any substance intended for use in the diagnosis, cure, mitigation, treatment or prevention of disease or in the enhancement of desirable physical or mental development and conditions in a mammal.

Therapeutic entities for employment with the responsive nanoparticles described herein therefore include, but are not limited to, small molecule compounds, polypeptides, proteins, and nucleic acids, for example, as described herein (e.g., and for the formation of mixed polymer particles).

Examples of proteins include, but are not limited to, antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules.

Classes of therapeutic agents include, but are not limited to, pharmaceutically active compounds which can be loaded into a polymer particle include, but are not limited to, anti-AIDS substances, anti-cancer substances, antibiotics, immunosuppressants (e.g. cyclosporine), anti-viral substances, enzyme inhibitors, neurotoxins, opioids, hypnotics, antihistamines, tranquilizers, anti-convulsants, muscle relaxants and anti-Parkinson substances, anti-spasmodics and muscle contractants, miotics and anti-cholinergics, antiglaucoma compounds, anti-parasite and/or anti-protozoal compounds, antihypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

A more complete listing of classes of compounds suitable for loading into polymers using the present methods may be found in the Pharmazeutische Wirkstoffe (Von Kleemann et al. (eds) Stuttgart/New York, 1987, incorporated herein by reference). Examples of particular pharmaceutically active substances are presented below:

Anti-AIDS agents are agents used to treat or prevent Autoimmune Deficiency Syndrome (AIDS). Examples of such agents include, but are not limited to, CD4,3'-azido-3'-deoxythymidine (AZT), 9-(2-hydroxyethoxymethyl)-guanine acyclovir, phosphonoformic acid, 1-adamantanamine, peptide T, and 2',3' dideoxycytidine.

Anti-cancer agents are agents used to treat or prevent cancer. Examples of such substances include, but are not limited to, methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include, but are not limited to, penicillin, tetracycline, chloramphenicol, minocycline, doxycycline, vanomycin, bacitracin, kanamycin, neomycin, gentamycin, erythromicin and cephalosporins.

Anti-viral agents are agents capable of destroying or suppressing the replication of viruses. Examples of anti-viral agents include, but are not limited to, α-methyl-P-adamantane methylamine, 1,-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, and adenine arabinoside.

Enzyme inhibitors are agents which inhibit an enzymatic reaction. Examples of enzyme inhibitors include, but are not limited to, edrophonium chloride, N-methylphysostigmine, neostigmine bromide, physostigmine sulfate, tacrine HCl, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-initrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, L(−)-deprenyl HCl, D(+)-deprenyl HCl, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine PCMB), 8,9-dichloro-2,3,4,5-tetrahydro-1H-2-benzazepine hydrochloride, p-aminoglutethimide, R(+)-p-aminoglutethimide tartrate, S(−)-p-aminoglutethimide tartrate, 3-iodotyrosine, L(−)-alpha-methyltyrosine, D(+)L(−)-alpha-methyltyrosine, acetazolamide, dichlorophenamide, 6-hydroxy-2-benzothiazolesulfonamide, and allopurinol.

Neurotoxins are agents which have a toxic effect on the nervous system, e.g. nerve cells. Neurotoxins include, but are not limited to, adrenergic neurotoxins, cholinergic neurotoxins, dopaminergic neurotoxins, and other neurotoxins. Examples of adrenergic neurotoxins include, but are not limited to, N-(2-chloroethyl)-N-ethyl-2-bromobenzylamine hydrochloride. Examples of cholinergic neurotoxins include, but are not limited to, acetylethylcholine mustard hydrochloride. Examples of dopaminergic neurotoxins include, but are not limited to, 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide.

Opioids are agents having opiate like effects that are not derived from opium. Opioids include, but are not limited to, opioid agonists and opioid antagonists. Opioid agonists include, but are not limited to, codeine sulfate, fentanyl citrate, hydrocodone bitartrate, loperamide HCl, morphine sulfate, noscapine, norcodeine, normorphine, thebaine. Opioid antagonists include, but are not limited to, nor-binaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are agents which produce a hypnotic effect. Hypnotics include, but are not limited to, pentobarbital sodium, phenobarbital, secobarbital, thiopental and mixtures, thereof, heterocyclic hypnotics, dioxopiperidines, glutarimides, diethyl isovaleramide, α (alpha)-bromoisovaleryl urea, urethanes and disulfanes.

Antihistamines are agents which competitively inhibit the effects of histamines. Examples of antihistamines include, but are not limited to, pyrilamine, chlorpheniramine, tetrahydrazoline, and the like.

Lubricants are agents that increase the lubricity of the environment into which they are delivered. Examples of biologically active lubricants include, but are not limited to, water and saline.

Tranquilizers are agents which provide a tranquilizing effect. Examples of tranquilizers include, but are not limited to, chloropromazine, promazine, fluphenazine, reserpine, deserpidine, and meprobamate.

Anti-convulsants are agents which have an effect of preventing, reducing, or eliminating convulsions. Examples of such agents include, but are not limited to, primidone, phenyloin, valproate, Chk and ethosuximide.

Muscle relaxants and anti-Parkinson agents are agents which relax muscles or reduce or eliminate symptoms associated with Parkinson's disease. Examples of such agents include, but are not limited to, mephenesin, methocarbomal, cyclobenzaprine hydrochloride, trihexylphenidyl hydrochloride, levodopa/carbidopa, and biperiden.

Anti-spasmodics and muscle contractants are agents capable of preventing or relieving muscle spasms or contractions. Examples of such agents include, but are not limited to, atropine, scopolamine, oxyphenonium, and papaverine.

Miotics and anti-cholinergics are compounds which cause bronchodilation. Examples include, but are not limited to, echothiophate, pilocarpine, physostigmine salicylate, diisopropylfluorophosphate, epinephrine, neostigmine, carbachol, methacholine, bethanechol, and the like.

Anti-glaucoma agents include, but are not limited to, betaxalol, pilocarpine, timolol, timolol salts, and combinations of timolol, and/or its salts, with pilocarpine.

Anti-parasitic, anti-protozoal and anti-fungal agents include, but are not limited to, ivermectin, pyrimethamine, trisulfapyrimidine, clindamycin, amphotericin B, nystatin, flucytosine, natamycin, and miconazole.

Anti-hypertensives are agents capable of counteracting high blood pressure. Examples of such agents include, but are not limited to, alpha-methyldopa and the pivaloyloxyethyl ester of alpha-methyldopa.

Analgesics are agents capable of preventing, reducing, or relieving pain. Examples of analgesics include, but are not limited to, morphine sulfate, codeine sulfate, meperidine, and nalorphine.

Anti-pyretics are agents capable of relieving or reducing fever and anti-inflammatory agents are agents capable of counteracting or suppressing inflammation. Examples of such agents include, but are not limited to, aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are agents which have an anesthetic effect in a localized region. Examples of such anesthetics include, but are not limited to, procaine, lidocain, tetracaine and dibucaine.

Ophthalmics include, but are not limited to, diagnostic agents such as sodium fluorescein, rose bengal, methacholine, adrenaline, cocaine, and atropine. Ophthalmic surgical additives include, but are not limited to, alpha-chymotrypsin and hyaluronidase.

Prostaglandins are art recognized and are a class of naturally occurring chemically related, long-chain hydroxy fatty acids that have a variety of biological effects.

Anti-depressants are agents capable of preventing or relieving depression. Examples of anti-depressants include, but are not limited to, imipramine, amitriptyline, nortriptyline, protriptyline, desipramine, amoxapine, doxepin, maprotiline, tranylcypromine, pheneizine, and isocarboxazide.

Anti-psychotic substances are agents which modify psychotic behavior. Examples of such agents include, but are not limited to, phenothiazines, butyrophenones and thioxanthenes.

Anti-emetics are agents which prevent or alleviate nausea or vomiting. An example of such an agent includes, but is not limited to, dramamine.

In topical skin care applications, a variety of active agents may be advantageously employed. By way of example only suitable active agents which may be incorporated into the cosmetic composition include, but are not limited to, anti-aging active substances, anti-wrinkle active substances, hydrating or moisturizing or slimming active substances, depigmenting active substances, substances active against free radicals, anti-irritation active substances, sun protective active substances, anti-acne active substances, firming-up active substances, exfoliating active substances, emollient active substances, and active substances for the treating of skin disorders such as dermatitis and the like.

Imaging agents are agents capable of imaging a desired site in vivo, e.g. a tumor. Examples of imaging agents include, but are not limited to agents having a label which is detectable in vivo, e.g., antibodies, peptides, or affibody attached to fluorescent labels or superparamagnetic iron oxide nanoparticles (SPIONs). The term antibody includes whole antibodies or fragments thereof.

Specific targeting agents include agents capable of delivering a therapeutic agent to a desired site, e.g. tumor, and providing a therapeutic effect. Examples of targeting agents include, but are not limited to, agents which can carry toxins or other agents which provide beneficial effects. The targeting agent can be an antibody linked to a toxin, e.g. ricin A or an antibody linked to a drug.

Neurotransmitters are agents which are released from a neuron on excitation and travel to either inhibit or excite a target cell. Examples of neurotransmitters include, but are not limited to, dopamine, serotonin, Q-aminobutyric acid, norepinephrine, histamine, acetylcholine, and epinephrine.

Cell response modifiers are chemotactic factors such as platelet-derived growth factor (PDGF). Other examples of chemotactic factors include, but are not limited to, neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other examples of cell response modifiers include, but are not limited to, interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

As those skilled in the art will appreciate, the foregoing list is exemplary only. Because the polymer particles discloses herein are suited for application under a variety of physiological conditions, such that a wide variety of therapeutic agents may be loaded into the polymer particles described herein and administered.

Referring to FIG. 1, an embodiment includes biodegradable, crosslinked PEG-coated P(LLA-HEMA) nanoparticles by free-radical dispersion polymerization using redox or thermal initiators. A similar scheme can be prepared for P(PCL-HEMA) nanoparticles by free-radical dispersion polymerization using redox or thermal initiators.

EXPERIMENTAL

1. Preparation of P(LLA-HEMA) Macromonomer
Materials

L(−) lactide (Polysciences, Inc.) was recrystallized from toluene before use. 2-Hydroxyethyl methacrylate (HEMA) (Aldrich, 97%) was dried over molecular sieves (4 Å) for 24 hours and distilled under negative pressure before use. Stannous octoate (Sigma, 95%), was used as received. Toluene (Acros, 99%) was refluxed over calcium hydride for one hour and distilled prior to use. Phosphorous pentoxide (Aldrich, 97%) used as a drying agent was also used as received.

Example 1

Synthesis of Methacrylate Terminated Poly(lactide) (PLA) Macromonomer ($85_{LLA}:15_{HEMA}$)

Methacrylate terminated macromonomer was prepared by the ring-opening polymerization of L-lactide in the presence of HEMA as initiator and stannous octoate as catalyst using a modified published method. Briefly, L-lactide (6.0234 g, 0.0418 mole), HEMA (900 μL, 0.00738 mole) and 3 drops of stannous octoate were placed in a 50 mL round-bottom flask equipped with a magnetic stir bar. The reaction flask was kept under vacuum for 10 minutes and polymerization was carried out in an inert atmosphere by flushing the flask with nitrogen gas for 24-38 hours on a silicone oil bath kept at 80-160° C., as in FIG. 1-A.

The polymer mass was dissolved in chloroform and extracted with 0.1M HCl to remove the catalyst followed by washing with deionized water. The pure polymer dissolved in the organic layer was then precipitated with excess cold methanol, collected by filtration and dried in a vacuum oven at room temperature under reduced pressure (25 in Hg, US gauge) over phosphorous pentoxide for 24 hours.

Characterization of P(LLA-HEMA) Macromonomer

Figure 2:
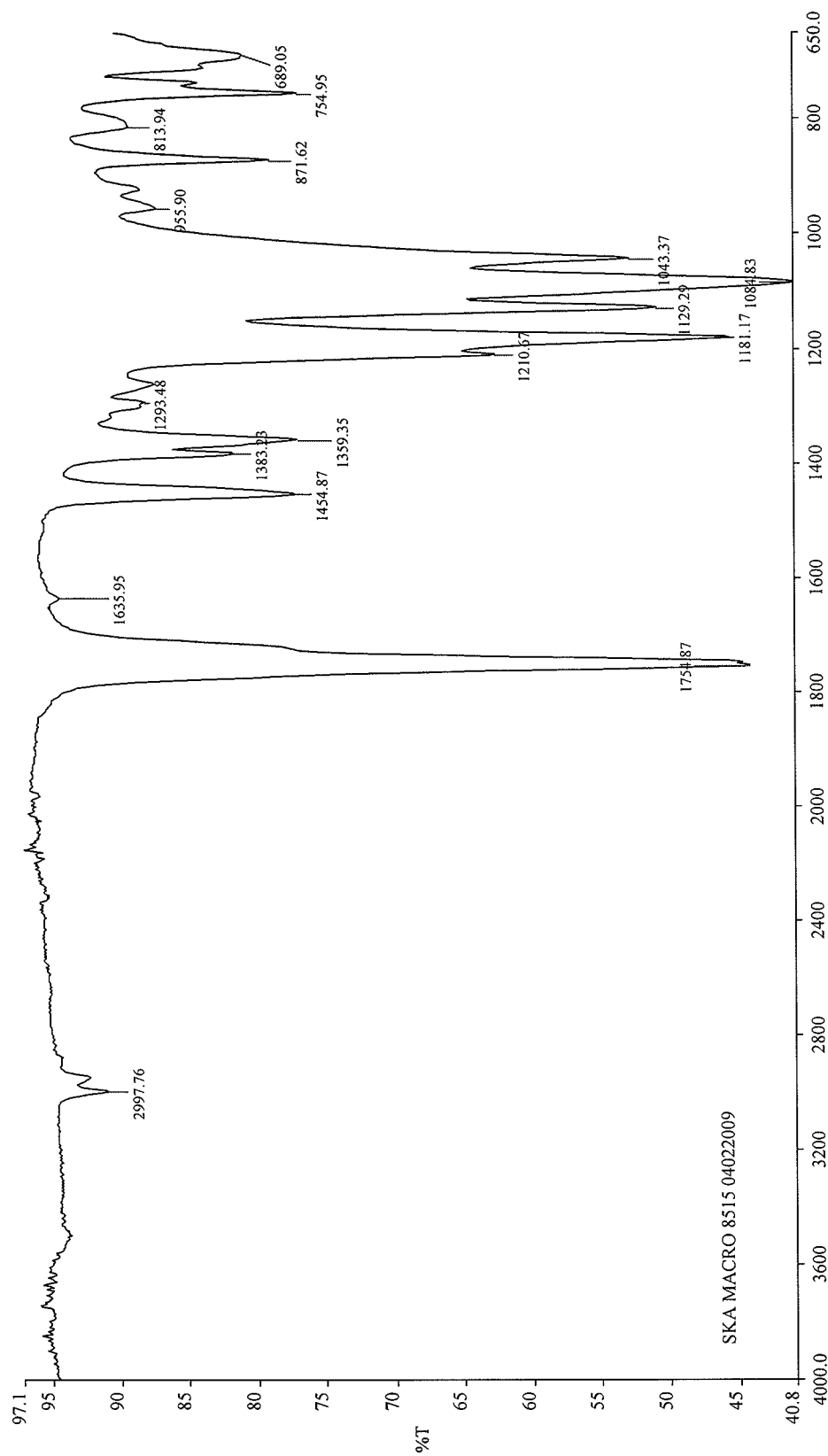
FIG. 2 is an infrared spectrum of P(LLA-HEMA) macromonomer.
Figure 3:
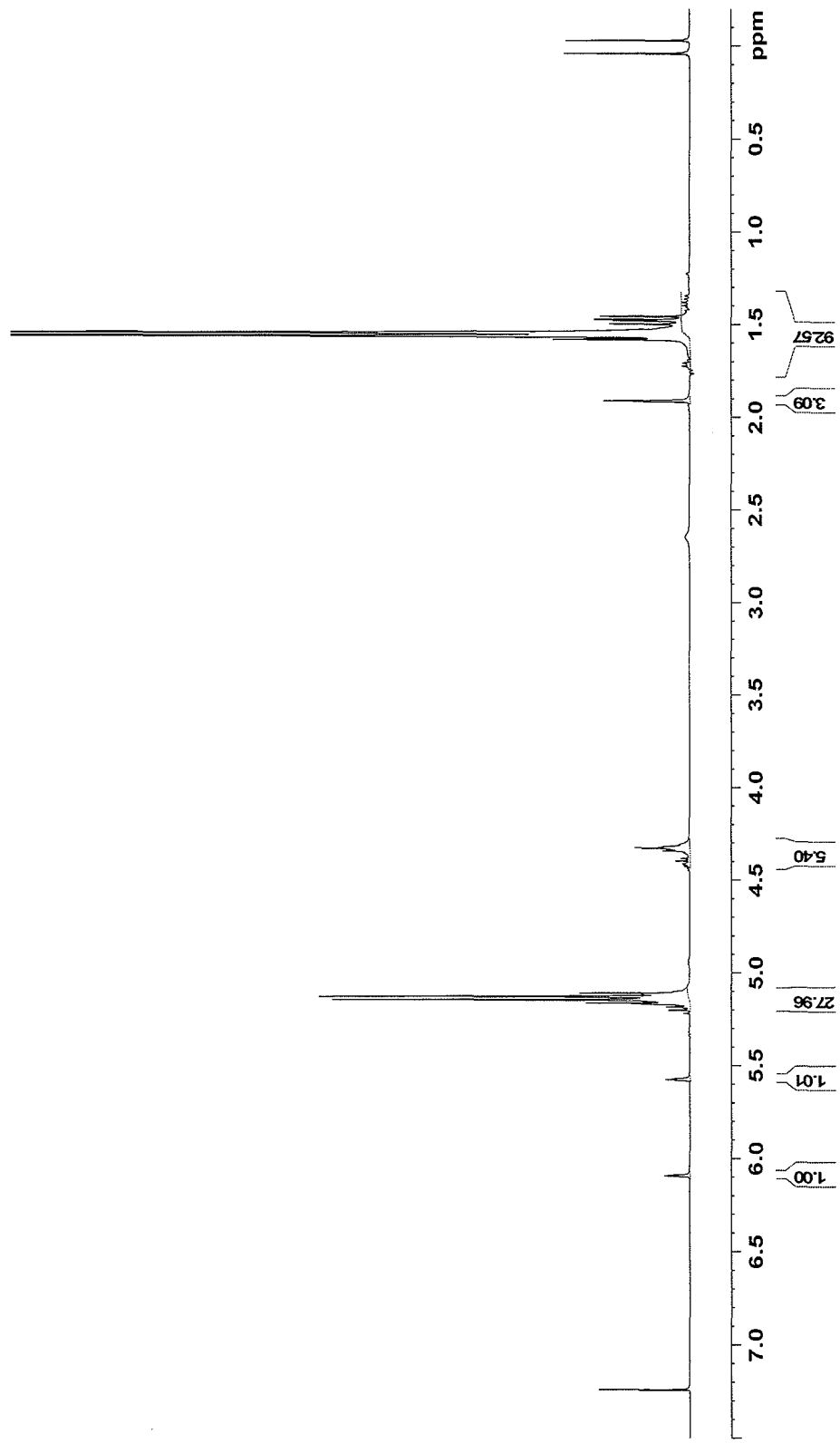
FIG. 3 is a proton NMR Spectrum of P(LLA-HEMA) macromonomer.

FT-IR spectrophotometric analysis of the synthesized macromonomer was carried out using a Perkin Elmer Spectrum 100 FT-IR spectrometer (FIG. 2). $^1$H NMR spectrophotometric analysis of the synthesized macromonomer in CDCl$_3$ was done on a Bruker AVANCE 400 MHz NMR spectrophotometer (FIG. 3). Table 1 shows the composition and other properties of the macromonomer.

Synthesis of Crosslinking Agent (MANHOMA)

MANHOMA was synthesized by methacryloylation of hydroxylamine. To describe the procedure, 2.5 g (0.036 mole) of hydroxylamine hydrochloride was dissolved in 26.1 mL (0.3298 mole) of pyridine. 8.3 mL (0.085 mole) of methacryloyl chloride and 9.5 mL of chloroform was added to the reaction mixture and stirred at 5° C. for 40 minutes and for 2 hours at room temperature. 28.4 mL of chloroform was then added to the reaction mixture and stirred until soluble. The resulting solution was washed twice with 47.3 mL (1.2 mole) of hydrochloric acid and the organic layer was washed twice with 40 mL of distilled water and dried with anhydrous magnesium sulphate. The oily product obtained after vacuum evaporation of the chloroform and subsequently diethyl ether was crystallized. See FIG. 1-B.

Characterization of the Crosslinking Agent

Figure 4:
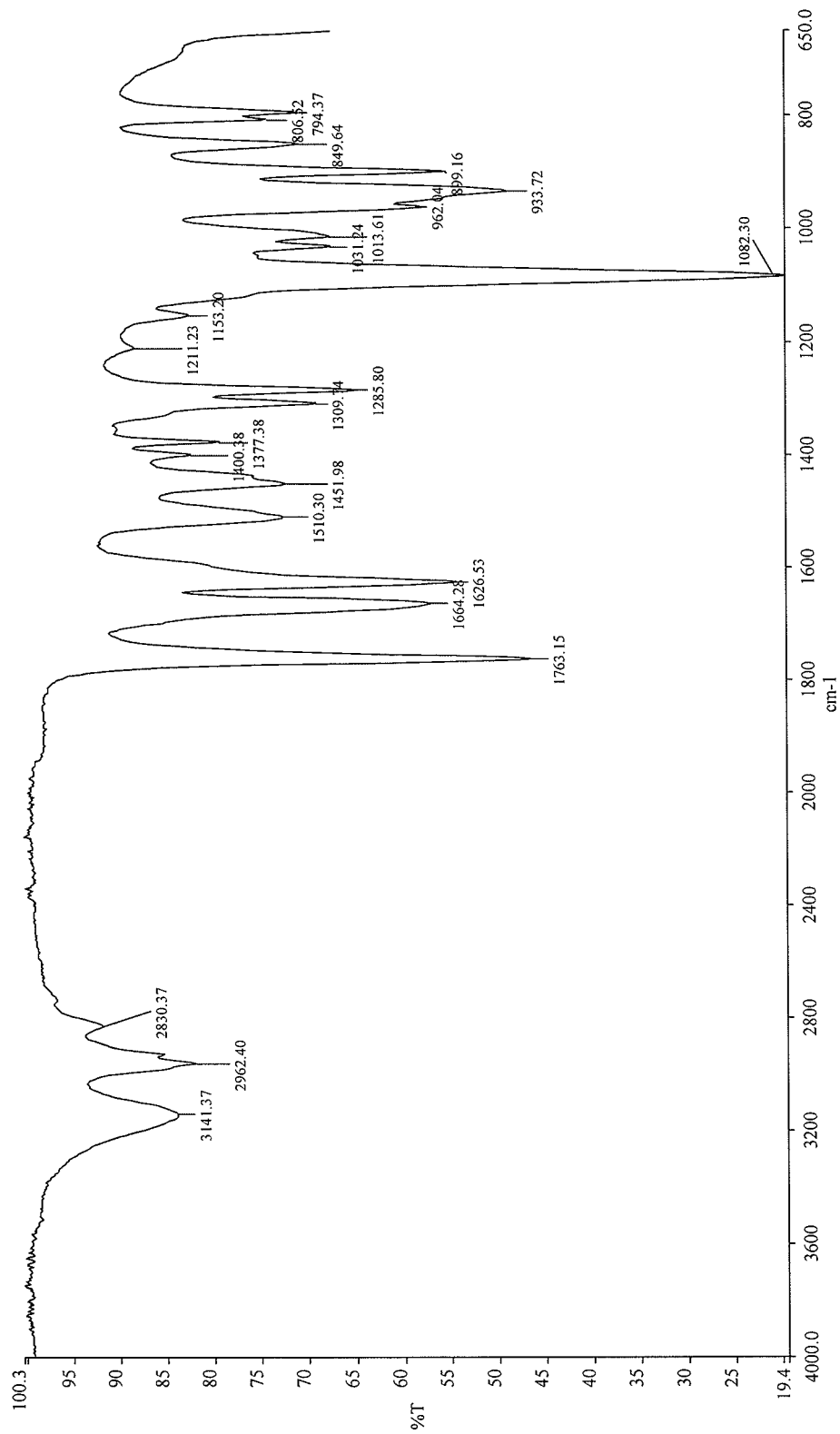
FIG. 4 is an IR spectrum of N,O-dimethacryloylhydroxylamine.
Figure 5:
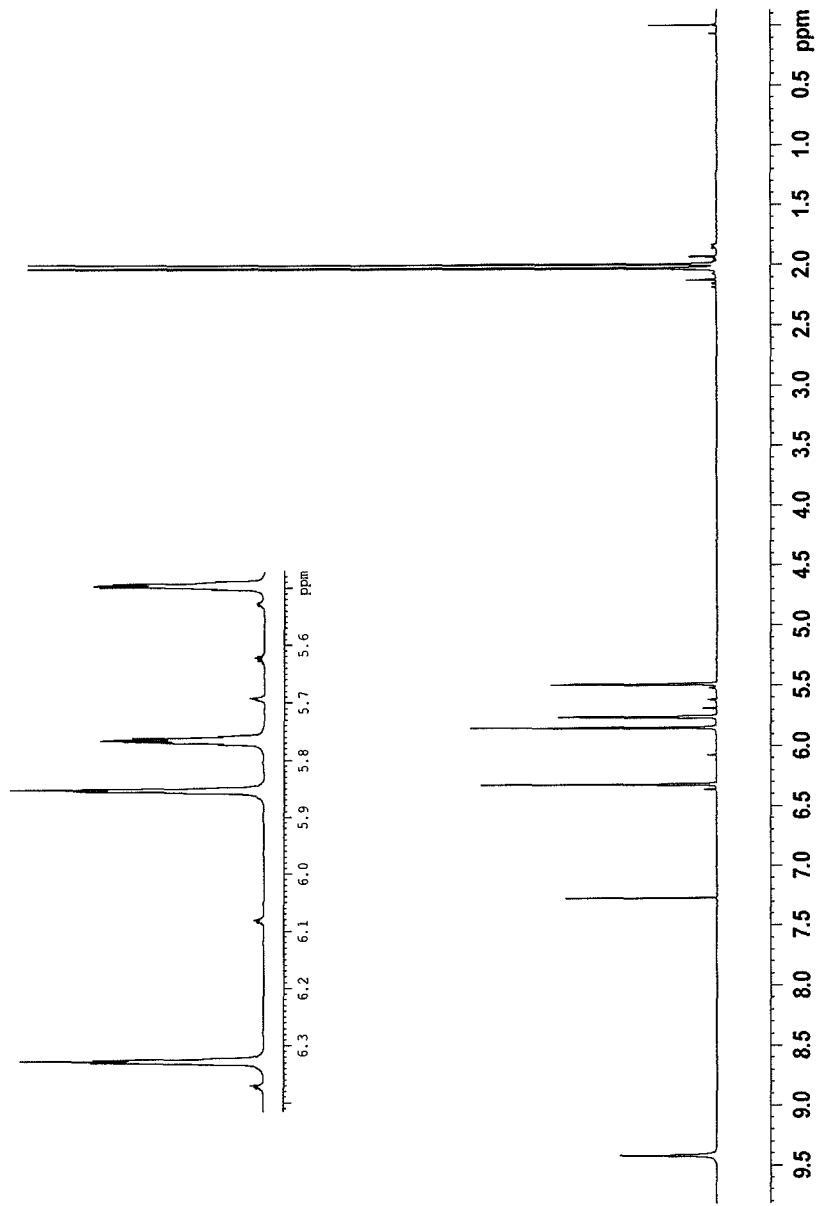
FIG. 5 is an $^1$H NMR spectrum of N,O-dimethacryloylhydroxylamine.

FT-IR spectrophotometric analysis of the synthesized crosslinking agent was carried out using a Perkin Elmer Spectrum 100 FT-IR spectrometer. The spectrum (FIG. 4) shows the presence of C═C stretch at 1627 cm$^{-1}$. $^1$H NMR spectrophotometric analysis of the synthesized crosslinking agent in CDCl$_3$ was done using a Bruker AVANCE 400 MHz NMR spectrophotometer. The proton NMR spectrum of MANHOMA (FIG. 5) confirms the presence of a divinylic structure with a pair of olefinic protons at about δ=5.86 ppm and δ=6.33 ppm and the other at about δ=5.49 ppm and δ=5.76 ppm. Melting point analysis was determined to be 54±1° C. using a Thomas® Hoover Unimelt™ capillary melting point apparatus (Thomas Scientific, USA).

TABLE 1

Properties of Macromonomer

| Macromonomer (LLA:HEMA) | Mn (GPC) | Mw (GPC) | Mn ($^1$NMR) | Polydispersity | mol % HEMA ($^1$NMR) |
|---|---|---|---|---|---|
| 85:15 | 3420 | 4247 | 2085 | 1.24 | 3.7 |

Preparation of Blank, Crosslinked Stealth Nanospheres by Dispersion Polymerization.

The free radical is generated by the decomposition of BPO activated by tertiary amines as accelerators. More specifically, the amine component induces a BPO decomposition reaction that generates free radicals which initiates polymerization reactions. Also, factors known to affect particle characteristics (crosslinker, stabilizer, initiator) were varied to obtain a desired formulation using a statistical design suitable for this kind of experiments. The D-optimal statistical mixture design was used in the experiment. The most suitable formulation was selected and loaded with a hydrophobic drug (Paclitaxel). Thermal method based on AIBN can also be used to prepare the nanoparticles.

0.24 mmol of p(LLA-HEMA) macromonomer, 0.252 mmol of PEG-MMA macromonomer and 0.016 mmol of crosslinker (MANHOMA) were dissolved in a Dioxane:DMSO:Water (12:5:2.5) solvent system. 0.196 mmol of BPO and 0.196 mmol of NPDEA was injected at predetermined intervals through the rubber closure under continuous flushing with nitrogen gas and with continuous stirring at 400 rpm. For the non-crosslinked nanoparticle, 0.24 mmol of p(LLA-HEMA) macromonomer, and 0.252 mmol of PEG-MMA macromonomer were dissolved in a Dioxane:DMSO:Water (12:5:2.5) solvent system. 0.196 mmol of BPO and 0.196 mmol of NPDEA was injected at predetermined intervals through the rubber closure under continous flushing with nitrogen gas and with continous stirring at 400 rpm. The overall polymerization time was 24 hours. The resulting particles were recovered by washing and dialysis. For drug-loaded particles, the drug (hydrophobic) was dissolved in the organic phase containing the hydrophobic monomers and the nanospheres were recovered by centrifugation. Paclitaxel was used as a model hydrophobic drug.

Figure 6:
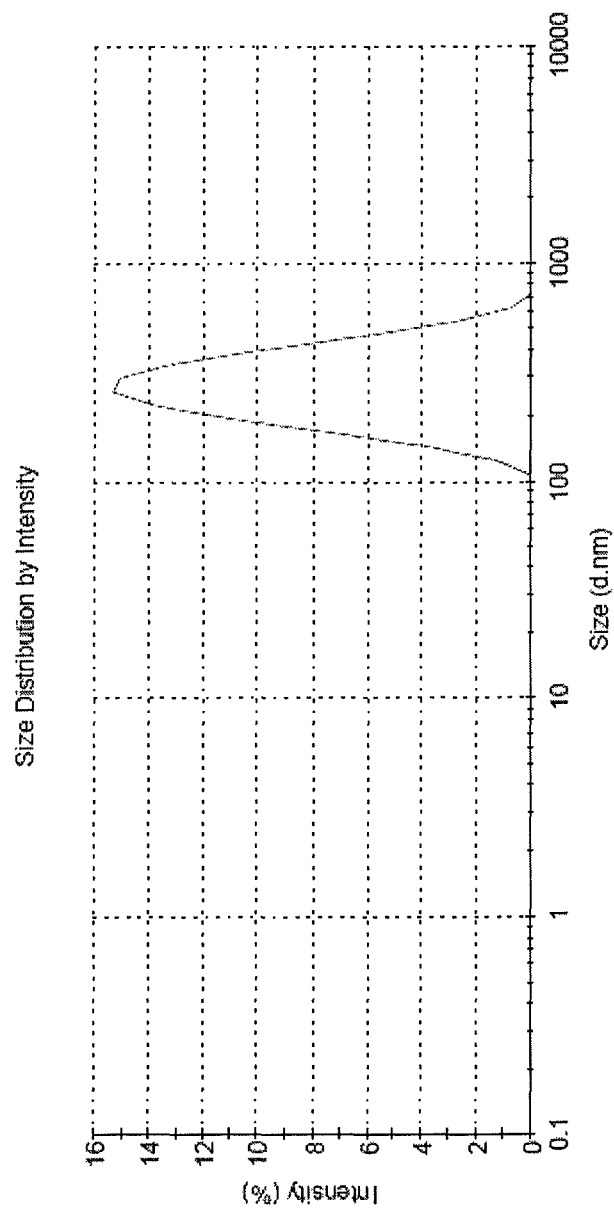
FIG. 6 is a particle size data by dynamic light scattering.

Characterization of Blank and Paclitaxel-loaded Particles (a) Particle Size and Size Distribution Analysis:

The average particle size was determined by dynamic light scattering using a Zetasizer Nano-ZS (Malvern Instruments, USA). The freeze-dried particles were redispersed in filtered deionized water using a probe sonicator before measurement. The mean of three measurements was recorded. The particle size distribution is given by the polydispersity index (PI). The mean particle size obtained was 244.2 nm (n=3) with a polydispersity index of 0.23 (n=3). Typical dynamic light scattering data is shown in FIG. 6.

(b) Zeta Potential Determination:

To evaluate the charge on the surface of the particles, the zeta potential was determined using the Zetasizer Nano-ZS (Malvern Instruments, USA) after suspending the particles in filtered deionized water. The mean of three measurements was recorded.

Figure 7:
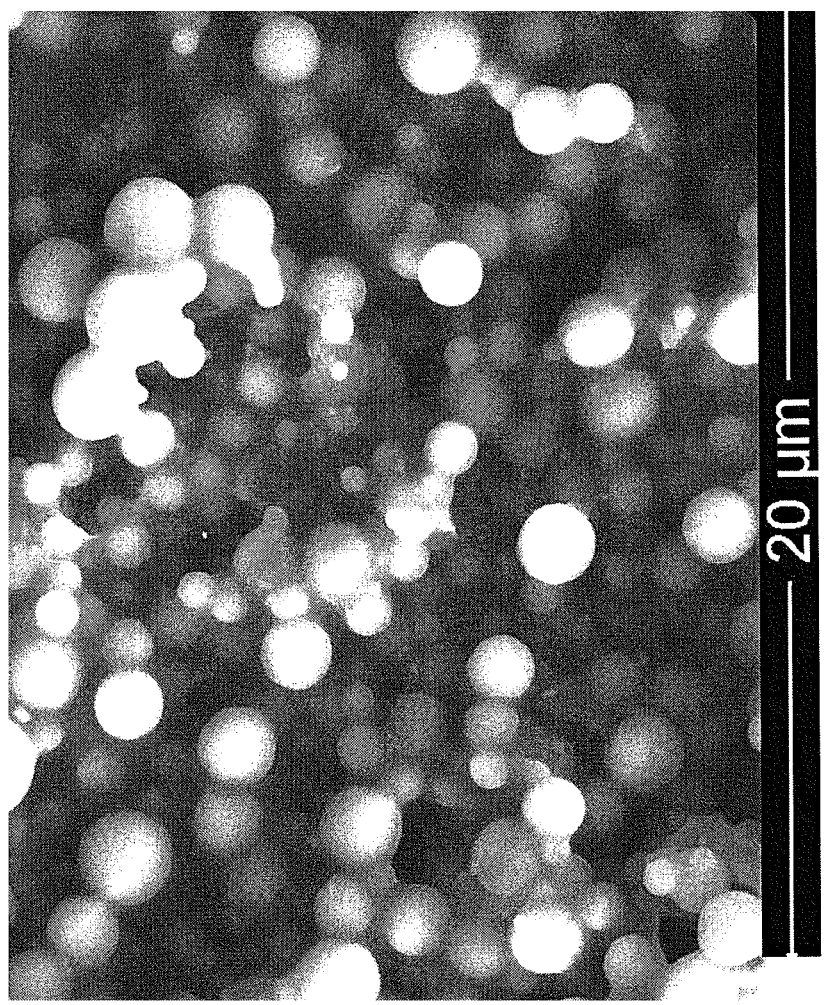
FIG. 7 is an SEM image of synthesized nanospheres.
Figure 8:
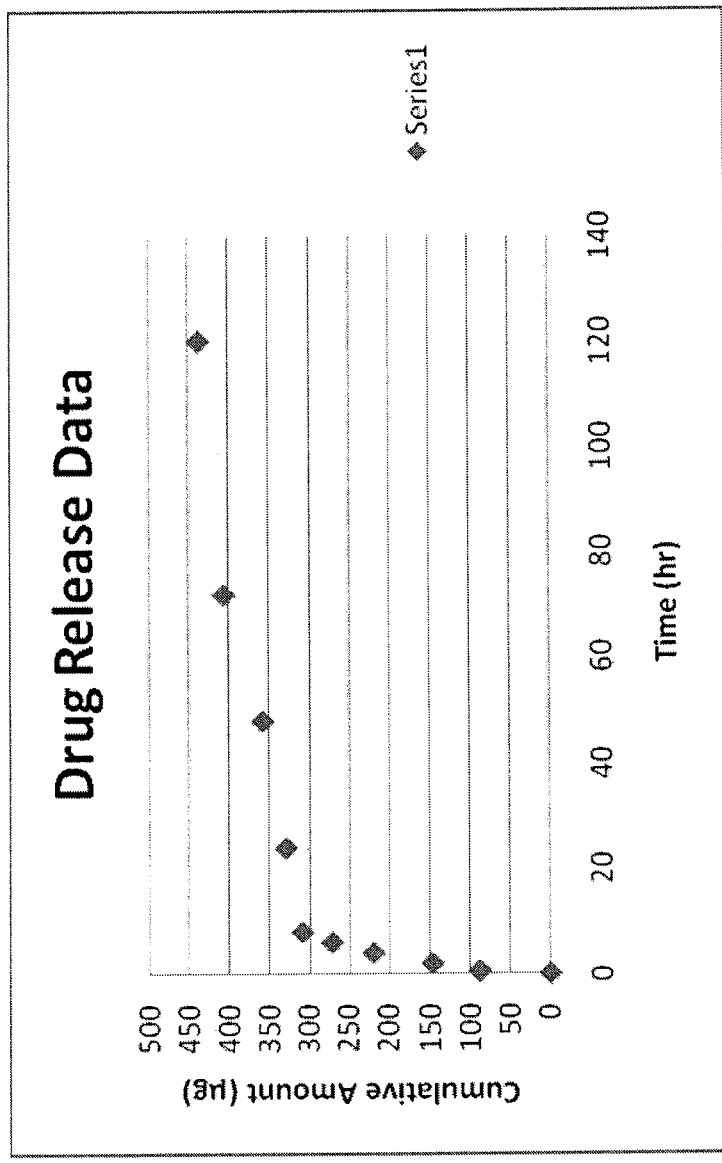
FIG. 8 is a cumulative amount released vs. time of paclitaxel-loaded nanoparticles.

(c) Scanning Electron Microscopy:

The surface morphology of the nanoparticles was evaluated using scanning electron microscopy (SEM) using the FEI Quanta 200F environmental scanning electron microscope. With this equipment, coating is not necessary which confers the advantage of accurate morphological features. SEM shows the formation of uniform, smooth spherical nanoparticles. The typical image is shown in FIG. 7.

Drug Loading and Encapsulation Efficiency:

Drug loading (the weight percent of paclitaxel in the nanoparticle formulation) and encapsulation efficiency (percentage of paclitaxel that is encapsulated out of the total used for nanoparticle preparation) were determined by high performance liquid chromatography (HPLC) in a HP series 1100 HPLC equipped with a Zorbax 300SB-C18 column kept at 37° C. using a 60:40 {acetonitrile: 12.5 mmol ammonium phosphate buffer (pH-4.5)} at a flow rate of 1 mL/min. A calibration curve was made using pure paclitaxel under the same conditions.

Encapsulation efficiency (EE) was determined by quantifying the amount of paclitaxel in the washings ($A_{wash}$) by HPLC and assuming that the rest of the drug used for nanoparticle preparation ($A_{prep}$) had been encapsulated. 3 mL of washings was extracted twice with 3 ml quantities of 1-octanol. The amount of paclitaxel in the octanol layer was quantified by HPLC and the amount of paclitaxel in total volume of washing was determined. The EE obtained was 31.9% and was determined from the equation below:

$$EE = \frac{(A_{prep}) - (A_{wash}) \times 100\%}{(A_{prep})}$$

Drug loading (DL) was determined by dissolving 5 mg of paclitaxel-loaded nanoparticles in acetonitrile ($A_{NP}$) (insoluble fractions was filtered off) and quantifying the amount of paclitaxel dissolved in the solution ($A_{PIS}$) by HPLC. The percent DL obtained (0.25% w/w) was calculated from the equation below:

$$DL = \frac{(A_{PIS}) \times 100\%}{(A_{NP})}$$

(e) In Vitro Release Studies:

10 mg of paclitaxel-loaded nanospheres was dispersed in 10 mL of freshly prepared phosphate buffered saline (PBS) in a 15 mL conical tube with a screw cap. Due to the poor solubility of paclitaxel in PBS, 3 mL of 1-octanol was added to continuously extract the released drug and therefore maintain sink conditions. The tube was clamped to a tumbling shaker maintained at 37° C. in a laboratory oven. At different time intervals, the octanol layer was completely removed and replaced with a fresh 3 mL of 1-octanol. The removed octanol was analyzed by HPLC using the calibration curve to determine the amount of paclitaxel released. A plot of cumulative amount released vs time was plotted (FIG. 6).

(f) In Vitro Cytotoxicity Studies in Breast Cancer Cell Lines:

The cytotoxicity of paclitaxel-loaded nanoparticles was quantified by using the CellTiter-Glo® luminescent cell viability assay, and compared with that of free paclitaxel at the same drug concentration. The concentrations tested range from 2.5 nM to 120 nM. The experiment was carried out as follows: Cultured cells (MCF-7, SK-OV 3, and MDA-MB-231) were seeded in 96-well plates at a seeding density of 6000 cells/well/0.1 mL medium and allowed to attach for 24 hours. Cells were then treated with 100 µl of culture medium containing paclitaxel-loaded nanoparticles or paclitaxel in solution (medium containing <0.05% DMSO). To allow direct comparison, the amount of paclitaxel-loaded nanoparticles containing the same amount of paclitaxel as the paclitaxel in solution was used. Control cells were treated with medium only, medium with 0.05% DMSO, and medium containing blank nanoparticles at the highest concentration tested.

Figure 9:
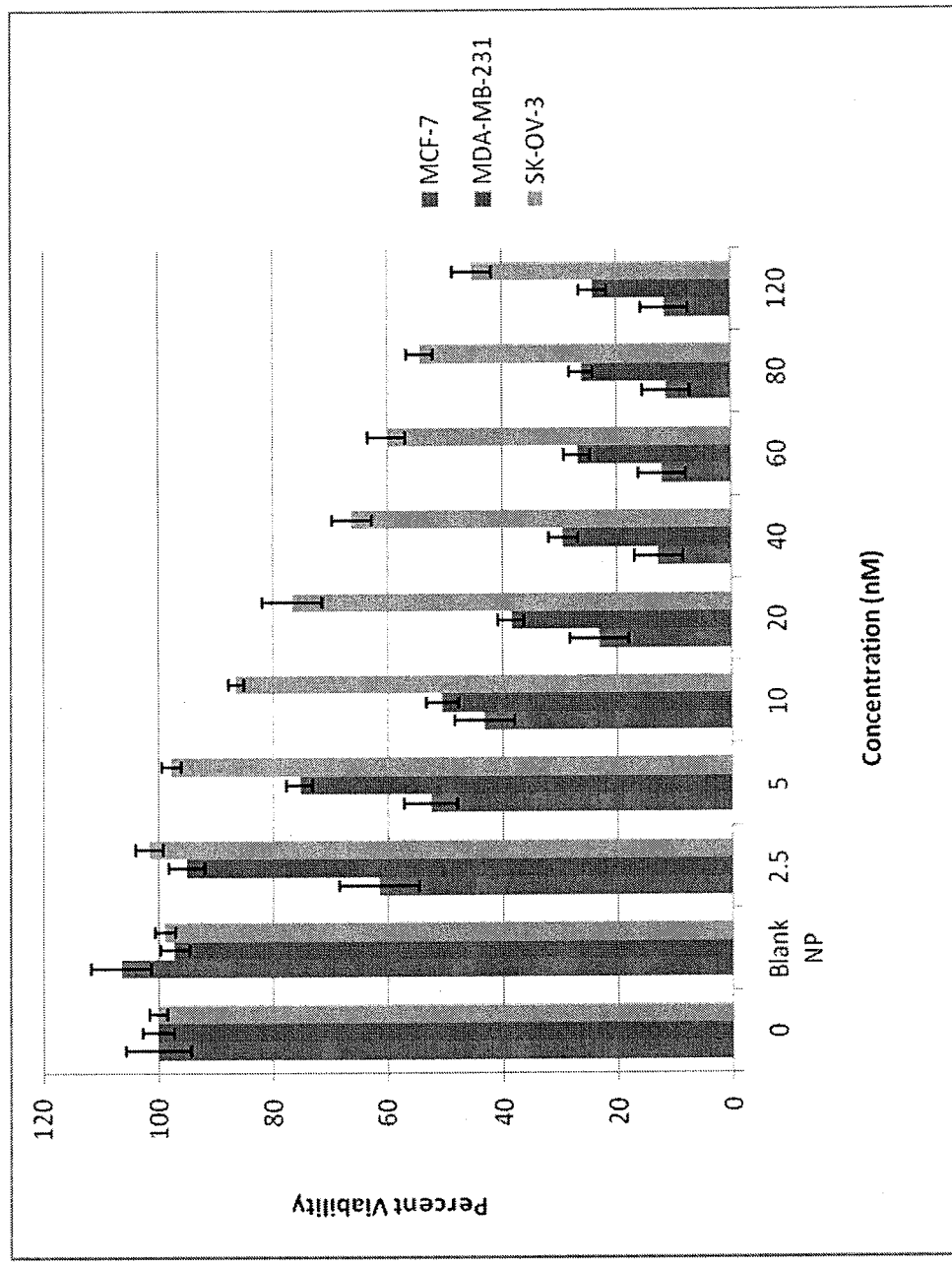
FIG. 9 shows the cytotoxicity of paclitaxel-loaded nanoparticles (NP) to MCF-7, MDA-MB-231 and SK-OV-3 cancer cells (96$h$ treatment) at different concentrations. The data in FIG. 9 is represented as mean±S.D. (n=4).

Cell viability was assessed at 48-, 72- and 96-hours post treatment respectively. Briefly, at the predetermined time intervals the treatment was washed off and fresh medium added. An amount of the CellTiter®-Glo reagent equal to the amount of medium was added. The plate was mixed by shaking on an orbital shaker for 2 minutes to induce cell lysis and luminescence was measured after 10 minutes using the FLUOstar OPTIMA plate reader (BMG LABTECH). In this assay, the number of viable cells in culture is determined by quantification of the ATP present which is an index of the presence of metabolically active cells (CellTiter®-Glo Luminescent Cell Viability Assay Technical Bulletin, TB 288; Promega). Results are presented as percent viability normalized to controls and represent the mean±S.D. of 4 replicates per concentration tested, as shown in FIG. 9. The results were analyzed by using Student's t-test using the SPSS® statistical software. Differences were considered significant at p<0.05.

Figure 10:
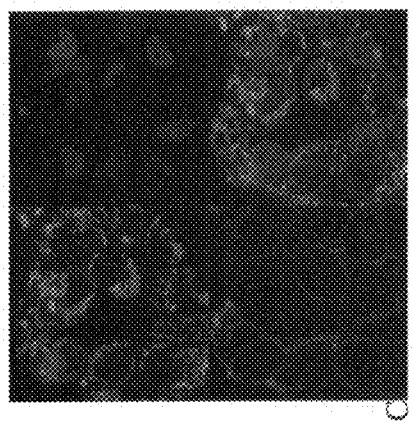
FIG. 10 shows the internalization of nanoparticles by MCF-7 cells (A) 1 hour; (B) 6 hours; and (C) 24 hours after incubation with fluorescent particles.
Figure 10:
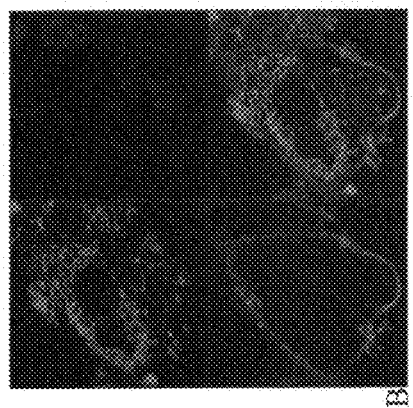
Figure 10:
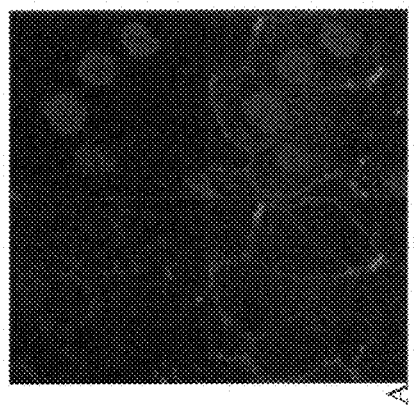

The characteristics of the cell lines used in this study are well known. All the three cell lines tested are sensitive to paclitaxel (Ofir et al., 2002; Tabuchi et al., 2009). For use as a drug carrier, polymeric nanoparticles must be biocompatible and biodegradable showing no toxic effects in vitro or in vivo (Ericco et al., 2009; Kunzmann, et al., 2010). Blank nanoparticles (synthesized without loading paclitaxel) showed no toxicity to cells at the highest concentration of drug-loaded nanoparticles tested for the longest duration of exposure tested (96 hours), as shown in FIG. 10. This show that they are biocompatible and that the cytotoxicity observed with paclitaxel-loaded nanoparticles is due to the encapsulated paclitaxel which suggest that they are suitable as a carrier for controlled delivery of drugs.

The cell viability assay shows that paclitaxel was released from the particles under study conditions and that both paclitaxel-loaded nanoparticles and the control paclitaxel solution inhibited cell growth in the cell lines used for the assay to relatively similar extents. Statistical analysis comparing viability of cells treated with blank nanoparticles to control cells (medium only) using the independent-samples T test show no significant difference in viability at 95% confidence interval (p=0.212; 0.068 and 0.049 for SK-OV-3 cells; MDA-MB-231 and MCF-7 respectively). The significance observed with MCF-7 cells is due to the greater proliferation of the cells in the presence of blank nanoparticles compared to control cells, as shown in FIG. 9. These results suggest that the paclitaxel-loaded particles can serve as an alternative to Taxol® without the attendant adverse effects.

(g) In Vitro Nanoparticle Uptake: Confocal Microscopy Studies:

It has been reported that drug-loaded nanoparticles can exhibit cytotoxicity by two main pathways; (i) by adsorbing to the cell membrane and releasing the drug which leads to the generation of a concentration gradient that would favor cellular drug influx by passive diffusion and (ii) by uptake into the cell by endocytosis leading to drug release in the interior of the cells (Jin et al., 2009; Al-Ghananeem et al., 2009). In the latter, the nanoparticles are retained in the cell cytoplasm for a prolonged period, acting as intracellular drug depots by slowly releasing the encapsulated drug. This leads to an increase in therapeutic efficacy for drugs such as paclitaxel that have the cytoplasm as their site of action by a sustained drug effect (Sahoo and Labhasetwar, 2005; Chavanpatil et al., 2006). To determine which of these two mechanisms is predominant and responsible for the observed cytotoxicity; cellular uptake was determined by confocal laser scanning microscopy (CLSM).

MCF-7 cells were seeded in glass-bottom microwell dishes with coverglass (MatTek Corp., MA, USA) at a seeding density of 600,000 cells/dish/1.5 mL medium and allowed to attach for 24 hours. After 24 hours, medium was replaced with 1 mL of rhodamine-123 loaded nanoparticles suspension in medium (1.71 mg/mL) and incubated. At different time points after nanoparticle incubation, Hoechst® 33342 (5 µg/mL) was added for 1 hour to stain the nucleus. Cells were then washed three times with PBS to remove nanoparticles that were not internalized and CellMask™ deep red plasma membrane stain (4 µg/mL) was added for 10 minutes at room temperature. The membrane stain was washed and the cells were observed with a confocal laser scanning microscope (CLSM 510, Carl Zeiss, GmbH) by using a 60×1.3 NA Plan-Apochromat oil immersion objective and a multitrack configuration. The Hoechst® 33342, rhodamine-123-loaded nanoparticles and CellMask™ deep red plasma membrane stain signals were collected by using BP 385-470 nm filter, 505-550 nm filter and LP 650 nm filter after excitation with the 364, 488, and 633 nm laser lines, respectively. Images (512×512 pixels) were acquired with line average of four by using the Zeiss AIM software at 1 h, 6 h, and 24 h after the administration of nanoparticles. Hoechst® 33342, Cell-Mask™ deep red and rhodamine-123 show blue, red and green color respectively.

Figure 11:
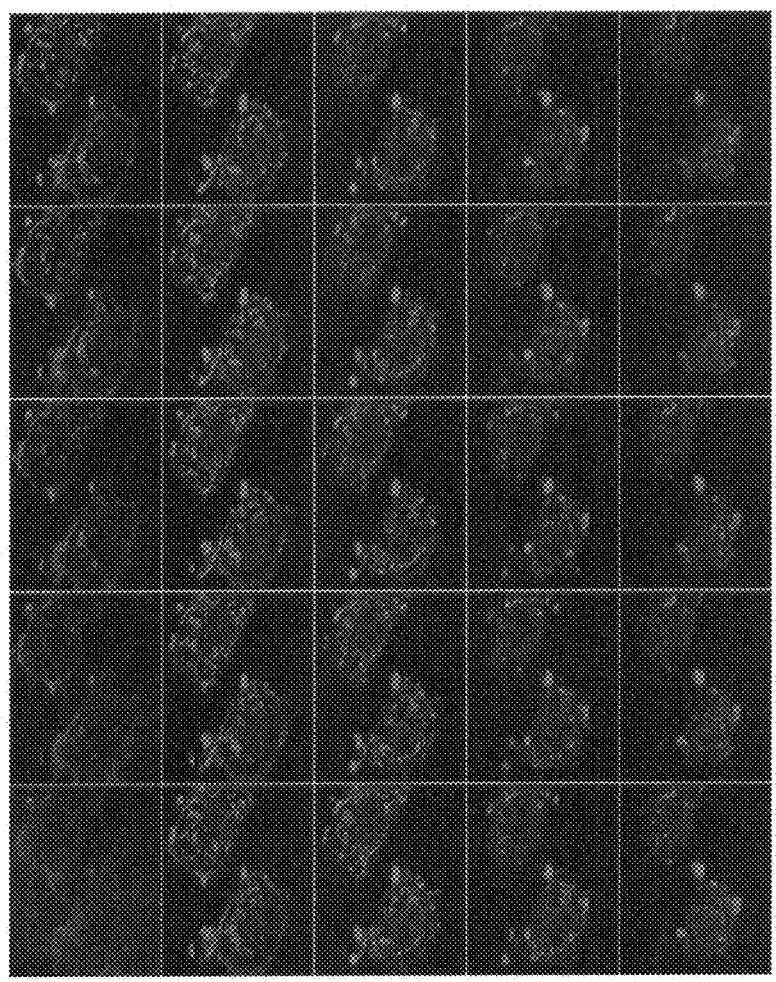
FIG. 11 shows Z-stack images confirming internalization of nanoparticles.

The cellular uptake of rhodamine-123 loaded nanoparticles was studied by confocal laser scanning microscopy. FIG. 10 shows the internalization of the nanoparticles in MCF-7 cells following exposure to the particles for 1, 6 and 24 hours respectively. The images show the rhodamine-123-loaded nanoparticles (colored green) aggregated and surrounding the nucleus stained blue (with Hoechst® 33342) and bound by the plasma membrane (stained red with the CellMask™ deep red plasma membrane stain). The images clearly show discrete nanoparticles within the cell membrane boundary. To further prove that the nanoparticles are taken up by the cell and not located on or adhering to the cell surface, Z-stacks (which are images of planes at various depths within the cell) confirm that the particles are within the cell, as shown in FIG. 11.

REFERENCES

1. Achilias Dimitris S. and Irini D. Sideridou, Kinetics of the benzoyl peroxide/amine initiated free-radical polymerization of dental dimethacrylate monomers: Experimental studies and mathematical modeling for TEGDMA and bis-EMA, *Macromolecules*, 37, 4254-65 (2004).
2. Akala Emmanuel O, Oluchi Elekwachi, Vantoria Chase, Hausalynn Johnson, Marjorie Lazarre, Kenneth Scott, Organic redox-initiated polymerization process for the fabrication of hydrogels for colon-specific drug delivery, *Drug Development and Industrial Pharmacy*, 29(4), 375-386 (2003).
3. Akala Emmanuel O., Pavla Kopeckova, Jindrich Kopecek, Novel pH-sensitive hydrogels with adjustable swelling kinetics; *Biomaterials*, 19, 1037-47 (1998).
4. Al-Ghananeem Abeer M., Malkawi Ahmad H., Muammer Yahya, Balko Justin M., Black Esther P., Mourad Walid and Romond Edward, Intratumoral Delivery of Paclitaxel in Solid Tumor from Biodegradable Hyaluronan Nanoparticle Formulations, *AAPS Pharm. Sci. Tech.*, 10(2), 410-417 (2009).
5. Allemann Eric, Eric Doelker and Robert Gurny, Drug loaded Poly(lactic acid) nanoparticles produced by a reversible salting out process: Purification of an injectable dosage form, *European Journal of Pharmaceutics and Biopharmaceutics*, 39(1), 13-18 (1993).
6. Athanasiou Kyriacos A., C. Mauli Agrawal, F. Alan Barber and Stephen S. Burkhart, Orthopaedic applications for PLA-PGA biodegradable polymers, *The Journal of Arthroscopy and Related Surgery*, 14(7), 726-737 (1998).
7. Boffa Lisa S, and Bruce M. Novak, Link-Functionalized Polymers: An unusual macromolecular architecture through bifunctional initiation, *Macromolecules*, 30, 3494-3506 (1997).
8. Cadee J. A, M. De Kerf, C. J. De Groot, W. Den Otter, W. E. Hennink, (Synthesis, characterization of 2-(mathacryloyloxy)-(di-) L-lactate and their application in dextran-based hydrogels, *Polymer*, 40, 6877-81 (1999).
9. Capek Ignac, Surface active properties of polyoxyethylene macromonomers and their role in radical polymerization in disperse systems, *Advances in Colloid and Interface Science*, 88(3), 295-357 (2000).
10. CellTiter®-Glo Luminescent Cell Viability Assay Technical Bulletin, TB 288, June 2009, Promega Corporation, WI, USA.
11. Chavanpatil Mahesh D., Patil Yogesh and Panyam Jayanth, Susceptibility of nanoparticle-encapsulated paclitaxel to P-glycoprotein-mediated drug efflux, *International Journal of Pharmaceutics*, 320, 150-156 (2006).
12. Czelusniak Izabela, Ezat Khosravi, Alan M. Kenwright, Christopher W. G. Ansell, Synthesis, Characterization, and Hydrolytic Degradation of Polylactide-Functionalized Polyoxanorbornenes, *Macromolecules*, 40, 1444-52 (2007).
13. Couvreur Patrick and Christine Vauthier, Nanotechnology: Intelligent design to treat complex disease, *Pharmaceutical Research*, 23(7), 1417-50 (2006).
14. Eguiburu Jose Luis, Maria Fernandez Berridi and Julio San Roman, Functionalization of poly(L-lactide) macromonomers by ring-opening polymerization of L-lactide initiated with hydroxyethyl methacrylate-aluminium alkoxides, *Polymer*, 36(1), 173-179 (1995).
15. Errico Cesare, Bartoli Cristina, Chiellini Federica and Chiellini Emo, Poly(hydroxyalkanoates)-based Polymeric Nanoparticles for Drug Delivery, *Journal of Biomedicine and Biotechnology,* 2009, Article ID 571702, 10 pages (2009).
15. Gerhardt Warren W., David E. Noga, Kenneth I. Hardcastle, Andres J. Garcia, David M. Collard, Marcus Weck, Functional Lactide Monomers: Methodology and Polymerization, *Biomacromolecules,* 7, 17-1742 (2006).
16. Gref. R., A. Domb, P. Quellec, T. Blunk, R. H. Muller, J. M. Verbavatz, R. Langer, The controlled intravenous delivery of drugs using PEG-coated sterically stabilized nanospheres, *Advanced Drug Delivery Reviews,* 16, 215-33 (1995).
17. Herault Damien, Christine Saluzzo, Marc Lemaire, Preparation of monodisperse enantiomerically pure glycidyl methacrylate-ethylene glycol dimethacrylate copolymers in dispersion copolymerization: Functionalization, *Reactive and Functional Polymers,* 66, 567-77 (2006).
18. Horak Daniel, Effect of reaction parameters on the particle size in the dispersion polymerization of 2-Hydroxyethyl Methacrylate, *Journal of Polymer Science Part A: Polymer Chemistry,* 37, 3785-92 (1999).
19. Horak Daniel and Ostap Chaykivskyy, Poly (2-Hydroxyethyl Methacrylate-co-N,O-Dimethacryloylhydroxylamine) particles by dispersion polymerization, *Journal of Polymer Science: Part A: Polymer Chemistry,* 40, 1625-1632 (2002).
20. Huang Samuel J. and John M. Onyari, Multicomponent polymers of poly(lactic acid) macromonomers with methacrylate terminal and copolymers of poly(2-hydroxyethyl methacrylate), *Journal of Macromolecular Science—Pure and Applied Chemistry A,* 33(5), 571-84 (1996).
21. Iojoiu Christina, David Cade, Hatem Fessi and Thierry Hamaide, Synthesis of oligocaprolactone vinyl ether macromonomers and their use for indomethacin encapsulation in polymer nanoparticles based on polycaprolactone macromonomer-maleic anhydride-N-vinyl pyrrolidone terpolymers, *Polymer International,* 55, 222-28 (2006).
22. Jin Cheng, Bai Ling, Wu Hong, Song Wenjie, Guo Guohen and Dou Kefeng, Cytotoxicity of Paclitaxel Incorporated in PLGA Nanoparticles on Hypoxic Human Tumor Cells, *Pharmaceutical Research,* 26(7), 1776-1784 (2009).
23. Kawaguchi Seigou and Koichi Ito, Dispersion Polymerization, *Advances in Polymer Science,* 175, 299-328 (2005).
24. Kim Jin-Woong, Chung-Hyuk Lee, Jung Bae Jun, Kyung-Do Suh, Monodisperse micron-sized crosslinked polystyrene particles: VII. Importance of monomer-diffusible surface characteristics of growing particles, *Colloids and Surfaces A: Physicochemical and Engineering Aspects,* 194, 57-64 (2001).
25. Kim So Yeon, I L Gyun Shin, Young Moo Lee, Chong Su Cho, Yong Kiel Sung, Methoxy poly(ethylene glycol) and ε-caprolactone amphiphilic block copolymeric micelle containing indomethacin. II. Micelle formation and drug release behaviours, *Journal of Controlled Release,* 51, 13-22 (1998).
26. Kim, Mi Sun, Gyu Ho Lee, Jae-Min Hong, Hyunjung Lee, Synthesis of Monodisperse PS-co-PDMS Microspheres by Dispersion Polymerization, *Materials Science and Engineering C,* 27, 1247-51 (2007).
27. Kiremitci-Gumusderelioglu Menemse and Gunday Deniz, Synthesis, Characterization and in Vitro Degradation of Poly(DL-lactide)/Poly (DL-lactide-co-glycolide) Films, *Turkish Journal of Chemistry,* 23, 153-161 (1999).
28. Kricheldorf Hans R., Kreiser-Saunders and Caroline Boettcher, Polylactones: 31. Sn(II)octoate-initiated polymerization of L-lactide: a mechanistic study, *Polymer,* 36(6), 1253-59 (1995).
29. Kunzmann Andrea, Andersson Britta, Thurnherr Tina, Krug Harald, Scheynius Annika, Fadeel Bengt, Toxicology of engineered nanomaterials: Focus on biocompatibility, biodistribution and biodegradation, *Biochimica et Biophysica Acta,* (e-published ahead of prining: doi:10.1016/j.bbagen.2010.04.007) (May 8, 2010).
30. Langer Robert, Polymer-Controlled Drug Delivery Systems, *Accounts of Chemical Research,* 26(10), 537-42 (1993).
31. Layre A., P. Couvreur, H. Chacun, J. Richard, C. Passirani, D. Requier, J. P. Benoit, R. Gref, Novel composite core-shell nanoparticles as busulfan carriers, *Journal of Controlled Release,* 111, 271-80 (2006).
32. Leobandung William, Hideki Ichikawa, Yoshinobu Fukumori, Nicholas A. Peppas, Monodisperse Nanoparticles of Poly(ethylene glycol) Macromers and N-Isopropyl Acrylamide for Biomedical Applications. Journal of Applied Polymer Science, 87, 1678-84 (2003).
33. Luo Weijun, Suming Li, Jianzhong Bei, Shenguo Wang, Synthesis and Characterization of Poly(L-lactide)-Poly (ethylene glycol) Multiblock Copolymers, *Journal of Applied Polymer Science,* 84, 1729-36 (2002).
34. McGee J. Paul, Stanley S. Davis, Derek T. O'Hagan, Zero order release of protein from poly (D,L-lactide-co-glycolide) microparticles prepared using a modified phase separation technique, *Journal of Controlled Release,* 34, 77-86 (1995).
35. Merkli A., C. Tabatabay, R. Gurny, J. Heller, Biodegradable polymers for the controlled release of ocular drugs, *Progress in Polymer Science,* 23, 563-80 (1998).
36. Metters A. T., K. S. Anseth, C. N. Bowman, Fundamental studies of a novel, biodegradable PEG-b-PLA hydrogel, *Polymer,* 41, 3993-4004 (2000).
37. Nair S. Lakshmi and Cato T. Laurencin, Biodegradable polymers as biomaterials, *Progress in Polymer Science,* 32, 762-98 (2007).
38. Ober Christopher K. and Kar P. Lok, Formation of large monodisperse copolymer particles by dispersion polymerization, *Macromolecules,* 20, 268-273 (1987).
39. Odian George, Principles of Polymerization Second ed.; Wiley-Interscience: New York, U.S.A., pp 194-204; 216-219; 271-275 (1981).
40. Ofir R, Seidman R, Rabinski T, Krup M, Yavelsky V, Weinstein Y and Wolfson M, *Cell Death and Differentiation,* 9, 636-642 (2002).
41. Ray Biswajit and Broja M. Mandal, Dispersion polymerization of Acrylamide: Part II. 2,2"-Azobisisobutyronitrile initiator, *Journal of Polymer Science: Part A: Polymer Chemistry,* 37, 493-499 (1999).
42. Ranade Vasant V., Drug delivery systems: 3B. Role of Polymers in Drug Delivery, *The Journal of Clinical Pharmacology,* 30, 107-120 (1990).
43. Ryner Maria, Anna Finne, Ann-Christine Albertsson, Hans R. Kricheldorf, L-lactide Macromonomer Synthesis Initiated by New Cyclic Tin Alkoxides Functionalized for Brushlike Structures, *Macromolecules,* 34, 7281-7287 (2001).
44. Sahoo Sanjeeb K. and Labhasetwar Vinod, Enhanced Antiproliferative Activity of Transferrin-Conjugated Paclitaxel-Loaded Nanoparticles is Mediated via Sus 45. Sairam Malladi, V. Ramesh Babu, Boya Vijaya Kumar Naidu, Tejraj M. Aminabhavi, Encapsulation efficiency and controlled release characteristics of crosslinked polyacrylamide particles, *International Journal of Pharmaceutics*, 320, 131-136 (2006).
46. Sarac A. S., Redox Polymerization, *Progress in Polymer Science*, 24, 1149-1204 (1999).
47. Sawhney Amarpreet S., Chandrashekhar P. Pathak and Jeffrey A. Hubbell, Bioerodible hydrogels based on photopolymerized poly(ethyleneglycol)-co-poly(α-hydroxy acid) diacrylate macromers, *Macromolecules*, 26:581-587 (1993).
48. Song, Jing-She, Frederic Tronc, Mitchell A. Winnik, Monodisperse, controlled micron-size dye-labeled polystyrene particles by two stage dispersion polymerization, *Polymer*, 47, 817-825 (2005).
49. Soppimath Kumaresh S., Tejraj M. Aminabhavi, Anandrao R. Kulkarni, Walter E. Rudzinski, Biodegradable polymeric nanoparticles as drug delivery devices, *Journal of Controlled Release*, 70, 1-20 (2001).
50. Tabuchi Yoko, Matsuoka Junji, Gunduz Mehmet, Imada Takako, Ono Ryoko, Ito Mitsuya, Motoki Takayuki, Yamatsuji Tomoki, Shirakawa Yasuhiro, Takaoka Munenori, Haisa Minoru, Tanaka Noriaki, Kurebayashi Junichi, Jordan V. Craig, Naomoto Yoshio, Resistance to paclitaxel therapy is related with Bcl-2 expression through an estrogen receptor mediated pathway in breast cancer, *International Journal of Oncology*, 34, 313-319 (2009).
51. Torchilin Vladimir, Multifunctional Nanocarriers, *Advanced Drug Delivery Reviews*, 58, 1532-1555 (2006).
52. Ulbrich K., V. Subr, P. Podperova, M. Buresova, Synthesis of novel hydrolytically degradable hydrogels for controlled drug release, *Journal of Controlled Release*, 34, 155-65 (1995).
53. Ulbrich K., V. Subr, L. W. Seymour, R. Duncan, Novel biodegradable hydrogels prepared using the divinylic crosslinking agent N,O-dimethacryloylhydroxylamine: 1. Synthesis and characterization of rates of gel degradation and rate of release of model drugs, in vitro and in vivo, *Journal of Controlled Release*, 24, 181-90 (1993).
54. Vazquez Blanca, Belen Levenfeld, Julio San Roman, Role of amine activators on the curing parameters, properties and tocixity of acrylic bone cements, *Polymer International*, 46, 241-50 (1998).
55. Wood David A., Biodegradable drug delivery systems, *International Journal of Pharmaceutics*, 7, 1-18 (1980).
56. Xu Peisheng, Edward A. Van Kirk, Shiyan Li, William J. Murdoch, Jun Ren, Muhammad Delwar Hussain, Maciej Radosz, Youquing Shen, Highly stable core-surface-crosslinked nanoparticles as cisplatin carriers for cancer chemotherapy, *Colloids and Surfaces B: Biointerfaces*, 48, 50-57.
57. Yang Tao, Fu-De Cui, Min-Koo Choi, Hongxia Lin, Suk-Jae Chung, Chang-Koo Shim, Dae-Duk Kim, Liposome Formulation of Paclitaxel with Enhanced Solubility and Stability, *Drug Delivery*, 14(5), 301-08.
58. Yin Wusheng, Emmanuel O. Akala, Robert E. Taylor, Design of naltrexone-loaded hydrolyzable crosslinked nanoparticles, *International Journal of Pharmaceutics*, 244, 9-19 (2002).
59. Zhao Yue, Jie Fu, Dennis K. P. Ng, Chi Wu, Formation and Degradation of Poly (D,L-lactide) Nanoparticles and Their Potential Application as Controllable Releasing Devices, *Macromolecular Bioscience*, 4, 901-06 (2004).

The invention claimed is:

1. A polymer particle which comprises a copolymer of poly(alklyene glycol-graft-lactate) which is a free radical polymerization product of polyalkylene glycol and polylactic acid, the polyalkylene glycol having been functionalized by an acrylate and the polylactic acid having been functionalized with a double bond, the poly(alklyene glycol-graft-lactate) optionally crosslinked by at least one hydrolysable monomer.

2. The polymer particle of claim 1, wherein the copolymer is poly(ethylene glycol-graft-P(LLA-HEMA)).

3. The polymer particle of claim 1, wherein the hydrolysable monomer is N,O-dimethacryloylhydroxylamine.

4. The polymer particle of claim 1, wherein a ratio of alklyene glycol to lactate is from about 0.25:1 to about 5:1.

5. The polymer particle of claim 1, wherein the amount of hydrolysable monomer is from about 0 mol % to about 10 mol % based on the total amount of copolymer.

6. The polymer particle of claim 1, wherein the average size is from about 50 nm to about 700.5 nm.

7. The polymer particle of claim 1, further comprising a therapeutic agent.

8. The polymer particle of claim 1, further comprising a therapeutic agent selected from the group consisting of paclitaxel, doxorubicin and docetaxel.

9. A polymer particle comprising a copolymer of:
(a) a hydrophobic monomer which comprises an alkene glycol acrylate and polylactic acid and which hydrophobic monomer includes a free radical polymerizable double bond,
(b) a hydrophilic monomer which comprises an alkene glycol acrylate which has been functionalized to include a free radical polymerizable double bond, and
(c) optionally a hydrolysable crosslinking agent.

10. The polymer particle of claim 9, wherein the hydrophilic monomer is a poly(ethylene glycol) monomethyl ether mono methacrylate.

11. The polymer particle of claim 9, wherein the hydrophobic monomer is P(LLA-HEMA) macromonomer.

12. The polymer particle of claim 9, wherein the hydrolysable crosslinking agent is N,O-dimethylacryloylhydroxylamine.

13. The polymer particle of claim 9, wherein a ratio of the hydrophilic monomer to the hydrophobic monomer is from about 0.25:1 to about 5:1.

14. The polymer particle of claim 9, wherein the amount of hydrolysable crosslinking agent is from about 0 mol % to about 10 mol % based on the total amount of the hydrophilic monomer and the hydrophobic monomer.

15. The polymer particle of claim 9, wherein the average size is from about 50 nm to about 700.5 nm.

16. The polymer of claim 9, further comprising a therapeutic agent.

17. The polymer particle of claim 9, further comprising a therapeutic agent selected from the group consisting of docetaxel, doxorubicin, and paclitaxel.

18. A polymer particle which comprises a polymer which is a free radical dispersion polymerization reaction product, the copolymer comprising structures represented by Formulas (I), (II), and optionally (III):

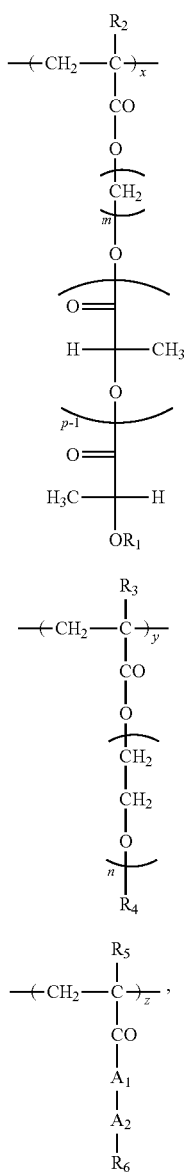

Formula (I)

Formula (II)

Formula (III)

wherein $R_2$-$R_5$ each represent a group, which may be the same or different from each other, and the group is selected from the group consisting of a hydrogen, a halogen, an alkyl group having one to five carbon atoms, wherein $R_1$ represents a group that is selected from the group consisting of hydrogen, a halogen, and an alkyl group having 1-20 carbon atoms, wherein $R_6$ represents another chain of the crosslinked polymer that is comprised of the structures represented by Formulas (I), (II), and (III), wherein x, y, and z represent an integer from 1 to 100, wherein n represents an integer 1 to 10,000, wherein $A_1$ is an oxygen atom or a secondary amine, where $A_2$ is an oxygen atom or a secondary amine, wherein m is an integer between 1-10, wherein p is an integer 1 to 10,000.

19. The polymer particle of claim 18, wherein $R_2$-$R_5$ each represent a methyl group and $R_1$ represents a hydrogen atom.

20. The polymer particle of claim 18, wherein a ratio of the structure represented by Formula (I) to Formula (II) is from about 1:0.25 to about 1:5.

21. The polymer particle of claim 18, the amount of Formula (I) relative to the amount of sum of Formulas (I), (II), and (III) is from about 0.2 mol % to about 1 mol % based on the total amount of copolymer.

22. The polymer particle of claim 18, wherein the average size is from about 50 nm to about 700.5 nm.

23. The polymer of claim 18, further comprising a therapeutic agent.

24. The polymer particle of claim 18, further comprising a therapeutic agent selected from the group consisting of docetaxel, doxorubicin, and paclitaxel.

25. The polymer particle of claim 7, wherein the therapeutic agent comprises from about 0.25 to about 5 weight percent of the polymer particle.

26. The polymer particle of claim 16, wherein the therapeutic agent is present in an amount which is greater than or equal to 0.25% w/w of the polymer particle.

27. A polymer particle which comprises a copolymer of poly(ethylene glycol-graft-P(LLA-HEMA)).

28. The polymer particle of claim 27 wherein the poly(ethylene glycol-graft-P(LLA-HEMA)) is crosslinked by at least one hydrolysable monomer.

29. The polymer particle of claim 27, further comprising a therapeutic agent.

30. The polymer particle of claim 28, further comprising a therapeutic agent.

31. The polymer particle of claim 29, wherein the therapeutic agent is present in an amount which is greater than or equal to 0.25% w/w of the polymer particle.

32. The polymer particle of claim 30, wherein the therapeutic agent is present in an amount which is greater than or equal to 0.25% w/w of the polymer particle.

33. A polymer particle which comprises a copolymer of poly(alklyene glycol-graft-lactate) which is a free radical polymerization product of polyalkylene glycol and polylactic acid both of which have been functionalized with double bonds, the poly(alklyene glycol-graft-lactate) optionally crosslinked by at least one hydrolysable monomer, wherein the copolymer of the poly(alklyene glycol-graft-lactate) includes structures represented by Formulas (I), (II), and optionally (III):

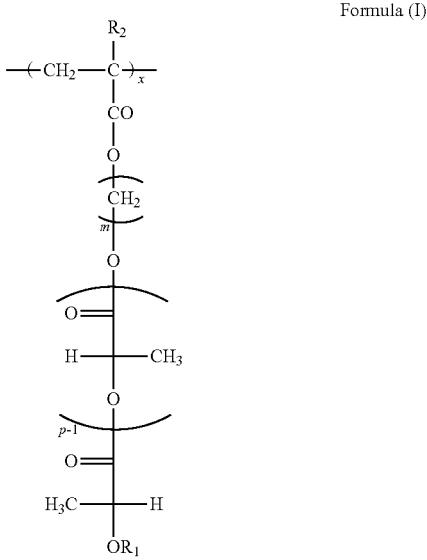

Formula (I)

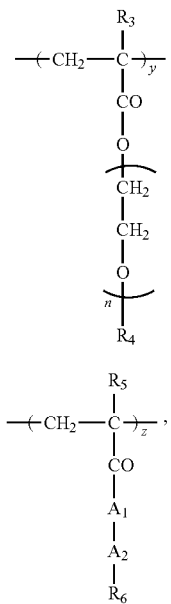

Formula (II)

Formula (III)

wherein $R_2$-$R_5$ each represent a group, which may be the same or different from each other, and the group is selected from the group consisting of a hydrogen, a halogen, an alkyl group having one to five carbon atoms, wherein $R_1$ represents a group that is selected from the group consisting of hydrogen, a halogen, and an alkyl group having 1-20 carbon atoms, wherein $R_6$ represents another chain of the crosslinked polymer that is comprised of the structures represented by Formulas (I), (II), and (III), wherein x, y, and z represent an integer from 1 to 100, wherein n represents an integer 1 to 10,000, wherein $A_1$ is an oxygen atom or a secondary amine, where $A_2$ is an oxygen atom or a secondary amine, wherein m is an integer between 1-10, wherein p is an integer 1 to 10,000.

34. The polymer particle of claim 1 wherein the polylactic acid has been functionalized with an acrylate.

35. The polymer particle of claim 9 wherein the polylactic acid has been functionalized with an acrylate.

36. The polymer particle of claim 33 wherein the polylactic acid has been functionalized with an acrylate.

* * * * *